United States Patent
Diallo et al.

(10) Patent No.: US 8,658,702 B2
(45) Date of Patent: Feb. 25, 2014

(54) SOLUBLE ANION EXCHANGERS FROM HYPERBRANCHED MACROMOLECULES

(76) Inventors: Mamadou Diallo, Pasadena, CA (US); Changjun Yu, Pasadena, CA (US)

(*) Notice: Subject to any disclaimer, the term of this patent is extended or adjusted under 35 U.S.C. 154(b) by 330 days.

(21) Appl. No.: 12/972,423

(22) Filed: Dec. 17, 2010

(65) Prior Publication Data

US 2011/0315636 A1 Dec. 29, 2011

Related U.S. Application Data

(60) Provisional application No. 61/287,648, filed on Dec. 17, 2009.

(51) Int. Cl.
*C08F 20/52* (2006.01)
(52) U.S. Cl.
USPC ........ 514/772.3; 424/400; 424/497; 424/498; 526/310; 528/328; 560/169
(58) Field of Classification Search
USPC ........... 560/169; 210/702; 424/400, 497, 498; 514/44, 772.3; 526/310; 528/328
See application file for complete search history.

(56) References Cited

U.S. PATENT DOCUMENTS

| | | | |
|---|---|---|---|
| 4,029,733 | A | 6/1977 | Faugeras et al. |
| 4,316,800 | A | 2/1982 | Stana et al. |
| 4,425,307 | A | 1/1984 | Devries |
| 4,599,400 | A | 7/1986 | Tomalia et al. |
| 5,041,516 | A | 8/1991 | Frechet et al. |
| 5,667,694 | A | 9/1997 | Cody et al. |
| 6,096,801 | A | 8/2000 | Vincent et al. |
| 6,464,971 | B1 | 10/2002 | Matthews et al. |
| 7,101,937 | B1 | 9/2006 | Frechet et al. |
| 7,470,369 | B2 | 12/2008 | Diallo |
| 2004/0048754 | A1 | 3/2004 | Herrmann et al. |
| 2005/0040109 | A1 | 2/2005 | Smith et al. |
| 2006/0205920 | A1 | 9/2006 | Dozol et al. |
| 2008/0200562 | A1* | 8/2008 | Yin et al. .................. 514/772.3 |
| 2008/0206183 | A1 | 8/2008 | Commeyras et al. |
| 2009/0001802 | A1 | 1/2009 | Diallo et al. |
| 2010/0181257 | A1 | 7/2010 | Frechet et al. |
| 2012/0035332 | A1 | 2/2012 | Diallo et al. |

FOREIGN PATENT DOCUMENTS

| | | |
|---|---|---|
| EP | 01 06 635 A1 | 4/1984 |
| GB | 2 338 958 A | 1/2000 |
| KR | 10-2008-0025157 A | 3/2008 |
| WO | 00/53649 A1 | 9/2000 |
| WO | 2004/076509 A2 | 9/2004 |
| WO | 2006/114528 A1 | 11/2006 |
| WO | 2006/114738 A2 | 11/2006 |

OTHER PUBLICATIONS

Chen et al., "Supramolecular Thermotropic Liquid Crystalline Materials with Nematic Mesophase Based on Methylated Hyperbranched Polyethylenimine and Mesogenic Carboxylic Acid", Macromolecular Rapid Communications, vol. 27, 2006, pp. 69-75.
Pastor-Perez et al., "Unprecedented Blue Intrinsic Photoluminescence from Hyperbranched and Linear Polyethylenimines: Polymer Architectures and pH-Effects", Macromolecular Rapid Communications, vol. 28, 2007, pp. 1404-1409.
Arkas et al., "Organic/Inorganic Hybrid Filters Based on Dendritic and Cyclodextrin "Nanosponges" for the Removal of Organic Pollutants from Water", Environmental Science & Technology, vol. 40, No. 8, 2006, pp. 2771-2777.
Hawker et al., "One-Step Synthesis of Hyperbranched Dendritic Polyesters", J. Am. Chem. Soc., vol. 113, No. 12, 1991, pp. 4583-4588.
Moyer et al., "Physical Factors in Anion Separations", Chapter 1 in Supramolecular Chemistry of Anions, edited by Bianchi et al., Wiley-VCH, 1997, pp. 1-44.
Kee et al., "Semi-Controlled Dendritic Structure Synthesis", Chapter 9 in Dendrimers and Other Dendritic Polymers, edited by J. M. J. Fréchet et al., John Wiley & Sons Ltd, 2001, pp. 209-236.
Krämer et al., "pH-Responsive Molecular Nanocarriers Based on Dendritic Core-Shell Architectures", Angew. Chem. Int. Ed., vol. 41, No. 22, 2002, pp. 4252-4256.
Chi et al., "Practical Synthesis of Enantiomerically Pure β2-Amino Acids via Proline-Catalyzed Diastereoselective Aminomethylation of Aldehydes", J. Am. Chem. Soc., vol. 129, 2007, pp. 6050-6055.
Roovers et al., "Dendrimers and Dendrimer-Polymer Hybrids", Advances in Polymer Science, vol. 142, 1999, pp. 179-228.
Martinez et al., "Dendritic Core-Shell Macromolecules Soluble in Supercritical Carbon Dioxide", Macromolecules, vol. 39, 2006, pp. 3978-3979.
Stevelmans et al., "Synthesis, Characterization, and Guest-Host Properties of Inverted Unimolecular Dendritic Micelles", J. Am. Chem. Soc. 1996, vol. 118, pp. 7398-7399.
Baek et al., "Core-Functionalized Star Polymers by Transition Metal-Catalyzed Living Radical Polymerization. 1. Synthesis and Characterization of Star Polymers with PMMA Arms and Amide Cores", Macromolecules, vol. 34, 2001, pp. 7629-7635.

(Continued)

*Primary Examiner* — Gregory Listvoyb
(74) *Attorney, Agent, or Firm* — Nixon Peabody LLP

(57) ABSTRACT

Novel macromolecules for filtering contaminants from water and non-aqueous solutions. Molecules such as polyethyleneimine (PEI) may be functionalized, cross-linked, and/or quaternized to improve their binding capacity or selectivity with particular water contaminants such as bromide, nitrate, and sulfate. The macromolecules may be either recyclable or non-recyclable, and may be recovered or separated from water using means such as ultrafiltration, flocculation, or immobilization on a substrate.

11 Claims, 36 Drawing Sheets

(56) References Cited

OTHER PUBLICATIONS

Yam et al., "Preparation, Characterization, Resistance to Protein Adsorption, and Specific Avidin-Biotin Binding of Poly(amidoamine) Dendrimers Functionalized with Oligo(ethylene glycol) on Gold", Journal of Colloid and Interface Science, vol. 296, 2006, pp. 118-130.

Vogtle et al., "Functional Dendrimers", Prog. Polym. Sci., vol. 25, 2000, pp. 987-1041.

Yang et al., "Polyethylene Glycol-Polyamidoamine Dendritic Micelle as Solubility Enhancer and the Effect of the Length of Polyethylene Glycol Arms on the Solubility of Pyrene in Water", Journal of Colloid and Interface Science, vol. 273, 2004, pp. 148-154.

Jal, P.K., "Chemical Modification of Silica Surface by Immobilization of Functional Groups for Extractive Concentration of Metal Ions", Talanta, vol. 62, 2004, pp. 1005-1028.

Reynhardt, Jan P. K., "Periodic Mesoporous Silica-Supported Recyclable Rhodium-Complexed Dendrimer Catalysts", Chem. Mater., vol. 16, 2004, pp. 4095-4102.

Vercruysse et al., "Synthesis and in Vitro Degradation of New Polyvalent Hydrasizde Cross-Linked Hydrogels of Hyaluronic Acid", Bioconjugate Chemistry (1997), 8(5), pp. 686-694, ISSN:1043-1802.

Fandel et al., "C02 Adsorption by PAMAM Dendrimers: Significant Effect of Impregnation into SBA-15", Microporous and Mesoporous Materials (Apr. 5, 2009), 123(1-3), pp. 140-149, ISSN: 1387-1811.

Lou et al., "Dehydrogenation of Tertiary Amines in Matrix-Assisted Laser Desorption/Ionizaiton Time-of-Flight Mass Spectrometry", Journal of Mass Spectrometry (2008), 43(8), pp. 1110-1122, ISSN: 1076-5174.

Kim et al., "Synthesis and Characterization of Poly(amino ester) for Slow Biodegradable Gene Delivery Vector", Bioorganic & Medicinal Chemistry (2007), 15(4), pp. 1708-1715, ISSN: 0968-0896.

Essawy et al., "Improving the Performance of Urea-Formaldehyde Wood Adhesive System Using Dendritic Poly(amiodoamine)s and Their Corresponding Half Generations", Journal of Applied Polymer Science, (Jun. 18, 2009), 114(2), pp. 1348-1355, ISSN: 0021-8995.

Diallo et al., "Dendritic Anion Hosts: Perchlorate Uptake by G5-NH2 Poly(propyleneimine) Dendrimer in Water and Model Electrolyte Solutions", Environmental Science & Technology, vol. 41, Nov. 18, 2007, 6521-6527.

Diallo et al., "Dendritic Chelating Agents. 1. Cu(II) Binding to Ethylene Diamine Core Poly(amidoamine) Dendrimers in Aqueous Solutions", American Chemical Society (2004), Langmuir, vol. 20, No. 7, 2004.

Diallo et al., "Dendritic Chelating Agents. 2. U(VI) Binding to Poly(amidoamine) and Poly(propyleneimine) Dendrimers in Aqueous Solutions", Environmental Science & Technology, vol. 42, No. 5, 2008, 1572-1579.

Gabelich et al., "Testing of Water Treatment Copolymers for Compatibility with Polyamide Reverse Osmosis Membranes", Environmental Progress, vol. 24, No. 4, Dec. 2005.

International Search Report and Written Opinion in International Application No. PCT/US2008/06578, dated Feb. 4, 2009.

International Search Report and Written Opinion in International Application No. PCT/US2009/059464, dated May 4, 2010.

International Search Report and Written Opinion in International Application No. PCT/US2010/061176, mailed Oct. 31, 2011.

Office Action in U.S. Appl. No. 12/124,952, mailed Sep. 13, 2010 (Restriction).

Office Action in U.S. Appl. No. 12/573,708, mailed Dec. 21, 2011 (Restriction).

Office Action in U.S. Appl. No. 13/251,106, mailed Feb. 29, 2012 (Restriction).

Office Action in U.S. Appl. No. 12/573,708, mailed Mar. 13, 2012 (Restriction).

Office Action in U.S. Appl. No. 12/124,952, mailed Apr. 1, 2011.

Office Action in U.S. Appl. No. 12/124,952, mailed Nov. 2, 2010.

Office Action in U.S. Appl. No. 13/251,106, mailed Apr. 24, 2012.

Office Action in U.S. Appl. No. 13/251,106, mailed Aug. 9, 2012.

Notice of Allowance in U.S. Appl. No. 12/573,708, mailed on May 30, 2012.

Diallo et al., "Dendrimer Enhanced Ultrafiltration. 1. Recovery of Cu(II) from Aqueous Solutions Using PAMAM Dendrimers with Ethylene Diamine Core and Terminal NH2 Groups", Environmental Science & Technology, vol. 39, No. 5, 2005, 1366-1377.

\* cited by examiner

FIG. 21

Single Component (Captymer) Binding Studies Using Makeup Water

| Captymer ID | Captymer Conc. in Solution (PPM) | PEI Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
|---|---|---|---|---|---|---|---|---|
| CJ14 | 0 | 0 | 323.83 | | 92.85 | | 21.81 | |
| New ITT makeup water pH =7.1 | 8 | 0 | 324.51 | 0.2% | 78.16 | -15.8% | 21.62 | -0.9% |
| | 16 | 0 | 326.45 | 0.8% | 63.01 | -32.1% | 21.58 | -1.1% |
| | 32 | 0 | 329.29 | 1.7% | 62.78 | -32.4% | 20.79 | -4.7% |
| | 64 | 0 | 337.20 | 4.1% | 62.20 | -33.0% | 20.62 | -5.5% |
| | 128 | 0 | 346.30 | 6.9% | 47.15 | -49.2% | 19.03 | -12.8% |
| | 160 | 0 | 347.74 | 7.4% | 43.45 | -53.2% | 18.79 | -13.8% |
| | 240 | 0 | 358.45 | 10.7% | 37.07 | -60.1% | 17.14 | -21.4% |

*FIG. 22*

| Single Component (Captymer) Binding Studies Using Makeup Water | | | | | | | | |
|---|---|---|---|---|---|---|---|---|
| Captymer ID | Captymer Conc. in Solution (PPM) | PEI Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ18 | 0 | 0 | 317.00 | | 86.70 | | 25.20 | |
| Makeup water at pH 7.1 | 7.5 | 0 | 308.50 | -2.7% | 68.70 | -20.8% | 23.20 | -7.9% |
| | 15 | 0 | 317.30 | 0.1% | 70.40 | -18.8% | 23.20 | -7.9% |
| | 30 | 0 | 316.60 | -0.1% | 67.40 | -22.3% | 23.20 | -7.9% |
| | 60 | 0 | 334.50 | 5.5% | 60.20 | -30.6% | 23.30 | -7.5% |
| | 120 | 0 | 352.40 | 11.2% | 36.40 | -58.0% | 23.20 | -7.9% |
| | 180 | 0 | 374.40 | 18.1% | 35.80 | -58.7% | 22.70 | -9.9% |
| | 240 | 0 | 382.90 | 20.8% | 25.10 | -71.0% | 21.50 | -14.7% |

FIG. 23

Single Component (Captymer) Binding Studies Using Makeup Water

| Captymer ID | Captymer Conc. in Solution (PPM) | PEI Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
|---|---|---|---|---|---|---|---|---|
| CJ20 | 0 | 0 | 326.60 | | 84.70 | | 24.40 | |
| Makeup water at pH 7.1 | 7.5 | 0 | 325.10 | -0.5% | 73.90 | -12.8% | 24.30 | -0.4% |
| | 15 | 0 | 322.90 | -1.1% | 65.70 | -22.4% | 24.00 | -1.6% |
| | 30 | 0 | 325.80 | -0.2% | 70.40 | -16.9% | 24.00 | -1.6% |
| | 60 | 0 | 332.80 | 1.9% | 59.60 | -29.6% | 23.70 | -2.9% |
| | 120 | 0 | 349.70 | 7.1% | 54.50 | -35.7% | 23.30 | -4.5% |
| | 180 | 0 | 356.50 | 9.2% | 46.70 | -44.9% | 22.10 | -9.4% |
| | 240 | 0 | 370.80 | 13.5% | 39.00 | -54.0% | 21.60 | -11.5% |

FIG. 24

| | Single Component (Captymer) Binding Studies Using Makeup Water | | | | | | | |
|---|---|---|---|---|---|---|---|---|
| Captymer ID | Captymer Conc. in Solution (PPM) | PEI Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ26 | *0* | *0* | 325.90 | | 94.80 | | 25.20 | |
| Makeup water at pH 7.1 | *7.5* | *0* | 325.30 | -0.2% | 86.90 | -8.3% | 25.00 | -0.8% |
| | *15* | *0* | 330.10 | 1.3% | 85.90 | -9.4% | 25.20 | 0.0% |
| | *30* | *0* | 323.10 | -0.9% | 81.40 | -14.1% | 24.10 | -4.4% |
| | *60* | *0* | 324.20 | -0.5% | 75.10 | -20.8% | 23.70 | -6.0% |
| | *120* | *0* | 348.10 | 6.8% | 73.50 | -22.5% | 24.10 | -4.4% |
| | *180* | *0* | 348.90 | 7.1% | 63.20 | -33.3% | 24.00 | -4.8% |
| | *240* | *0* | 354.10 | 8.7% | 49.70 | -47.6% | 21.80 | -13.5% |

*FIG. 25*

| | Single Component (Captymer) Binding Studies Using Makeup Water | | | | | | | |
|---|---|---|---|---|---|---|---|---|
| Captymer ID | Captymer Conc. in Solution (PPM) | PEI Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ28 | *0* | *0* | 325.23 | | 95.26 | | 21.16 | |
| New ITT makeup water at pH 7.1 | *8* | *0* | 321.20 | -1.2% | 75.84 | -20.4% | 20.54 | -2.9% |
| | *16* | *0* | 320.99 | -1.3% | 82.56 | -13.3% | 19.64 | -7.2% |
| | *32* | *0* | 318.78 | -2.0% | 81.14 | -14.8% | 19.59 | -7.4% |
| | *64* | *0* | 309.20 | -4.9% | 79.29 | -16.8% | 19.03 | -10.1% |
| | *128* | *0* | 308.83 | -5.0% | 72.82 | -23.6% | 19.02 | -10.1% |
| | *160* | *0* | 295.65 | -9.1% | 71.94 | -24.5% | 19.03 | -10.1% |
| | *240* | *0* | 294.90 | -9.3% | 68.21 | -28.4% | 19.00 | -10.2% |

*FIG. 26*

| Dual Components [Captymer + Cross-linked PEI (AN-5)] Binding Studies Using Makeup Water | | | | | | | | |
|---|---|---|---|---|---|---|---|---|
| Captymer ID | Captymer Conc. in Solution (PPM) | AN-5 Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ14 | 0 | 0 | 325.11 | | 86.676 | | 19.42083 | |
| New ITT | 128 | 16 | 342.34 | 5.3% | 52.31 | -39.6% | 17.23 | -11.3% |
| Makeup water | 128 | 64 | 392.99 | 20.9% | 28.58 | -67.0% | 16.97 | -12.6% |
| at pH 7.1 | 128 | 128 | 415.46 | 27.8% | 15.48 | -82.1% | 16.79 | -13.5% |
| | 128 | 240 | 435.11 | 33.8% | 11.37 | -86.9% | 14.83 | -23.7% |

*FIG. 27*

| Dual Components [Captymer + Cross-linked PEI (AN-5)] Binding Studies Using Makeup Water ||||||||
|---|---|---|---|---|---|---|---|
| Captymer ID | Captymer Conc. in Solution (PPM) | AN-5 Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ18 | 0 | 0 | 327.62 | | 80.45 | | 23.23 | |
| Makeup water at pH 7.1 | 128 | 16 | 364.55 | 11.3% | 31.52 | -60.8% | 21.83 | -6.0% |
| | 128 | 64 | 387.02 | 18.1% | 15.96 | -80.2% | 20.81 | -10.4% |
| | 128 | 128 | 401.78 | 22.6% | 6.78 | -91.6% | 19.91 | -14.3% |
| | 128 | 240 | 408.92 | 24.8% | 7.66 | -90.5% | 17.38 | -25.2% |
| | 128 | 480 | 431.40 | 31.7% | 5.76 | -92.8% | 15.14 | -34.8% |

FIG. 28

| Dual Components [Captymer + Cross-linked PEI (AN-5)] Binding Studies Using Makeup Water | | | | | | | | |
|---|---|---|---|---|---|---|---|---|
| Captymer ID | Captymer Conc. in Solution (PPM) | AN-5 Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ20 | | | | | | | | |
| Makeup water at pH 7.1 | 0 | 0 | 325.97 | | 90.13 | | 24.42 | |
| | 128 | 16 | 327.77 | 0.6% | 33.02 | -63.4% | 21.53 | -11.8% |
| | 128 | 64 | 345.20 | 5.9% | 32.24 | -64.2% | 21.03 | -13.9% |
| | 128 | 128 | 392.46 | 20.4% | 13.57 | -84.9% | 20.62 | -15.6% |
| | 128 | 240 | 410.26 | 25.9% | 10.06 | -88.8% | 18.84 | -22.8% |
| | 128 | 480 | 442.20 | 35.7% | 5.63 | -93.8% | 16.41 | -32.8% |

FIG. 29

| Dual Components [Captymer + Cross-linked PEI (AN-5)] Binding Studies Using Makeup Water |||||||||
|---|---|---|---|---|---|---|---|---|
| Captymer ID | Captymer Conc. in Solution (PPM) | AN-5 Conc. in Solution (PPM) | Chloride Actual Conc. (ppm) | % Change From Initial Conc. | Sulfate Actual Conc. (ppm) | % Change From Initial Conc. | Nitrate Actual Conc. (ppm) | % Change From Initial Conc. |
| CJ26 | 0 | 0 | 332.72 | | 82.97 | | 24.05 | |
| Makeup water at pH 7.1 | 128 | 16 | 379.59 | 14.1% | 45.66 | -45.0% | 23.68 | -1.5% |
| | 128 | 64 | 384.95 | 15.7% | 23.46 | -71.7% | 22.23 | -7.5% |
| | 128 | 128 | 404.76 | 21.7% | 9.81 | -88.2% | 21.23 | -11.7% |
| | 128 | 240 | 412.36 | 23.9% | 6.72 | -91.9% | 18.61 | -22.6% |
| | 128 | 480 | 441.53 | 32.7% | 7.99 | -90.4% | 16.06 | -33.2% |

*FIG. 30*

CJ40 to Makeup Water

| Sample ID | CJ40 Conc. in Solution (PPM) | Chloride Actual Conc. (ppm) | % Change From Initial Conc. in Chloride | Sulfate Actual Conc. (ppm) | % Change From Initial Conc. in Sulfate | Nitrate Actual Conc. (ppm) | % Change From Initial Conc. in Nitrate |
|---|---|---|---|---|---|---|---|
| A. Feed | 0 | 342.96 | | 102.47 | | 23.36 | |
| B | 8 | 344.11 | 0.33% | 99.99 | -2.41% | 23.35 | -0.02% |
| C | 16 | 347.29 | 1.26% | 80.68 | -21.26% | 23.32 | -0.17% |
| D | 32 | 348.88 | 1.73% | 77.88 | -24.00% | 23.30 | -0.23% |
| E | 64 | 371.30 | 8.26% | 54.43 | -46.88% | 23.06 | -1.28% |
| F | 128 | 398.37 | 16.16% | 37.87 | -63.05% | 22.87 | -2.10% |
| G | 160 | 406.77 | 18.60% | 29.21 | -71.50% | 21.48 | -8.01% |
| H | 240 | 407.14 | 18.71% | 29.02 | -71.68% | 21.18 | -9.32% |
| F | 480 | 466.54 | 36.03% | 10.44 | -89.81% | 21.07 | -9.77% |

FIG. 31

CJ14 and CJ40 to Makeup Water

| Sample ID | CJ40 Conc. in Solution (PPM) | CJ14 Conc. in Solution (PPM) | Chloride Actual Conc. (ppm) | % Change From Initial Conc. in Chloride | Sulfate Actual Conc. (ppm) | % Change From Initial Conc. in Sulfate | Nitrate Actual Conc. (ppm) | % Change From Initial Conc. in Nitrate |
|---|---|---|---|---|---|---|---|---|
| A. FEED | 0 | 0.00 | 352.27 | | 104.52 | | 23.84 | |
| B | 16 | 128.00 | 379.36 | 7.69% | 46.66 | -55.36% | 22.30 | -6.42% |
| C | 24 | 128.00 | 393.79 | 11.79% | 33.28 | -68.16% | 22.16 | -7.02% |
| D | 128 | 128.00 | 412.54 | 17.11% | 23.85 | -77.18% | 21.89 | -8.16% |
| E | 240 | 128.00 | 451.27 | 28.10% | 13.07 | -87.50% | 20.66 | -13.31% |
| F | 480 | 128.00 | 496.40 | 40.92% | 7.86 | -92.48% | 18.62 | -21.87% |

*FIG. 32*

CJ26 and CJ40 to Makeup Water ( adding CJ26 first and then CJ40)

| Sample ID | CJ40 Conc. in Solution (PPM) | CJ26 Conc. in Solution (PPM) | Chloride Actual Conc. (ppm) | % Change From Initial Conc. in Chloride | Sulfate Actual Conc. (ppm) | % Change From Initial Conc. in Sulfate | Nitrate Actual Conc. (ppm) | % Change From Initial Conc. in Nitrate |
|---|---|---|---|---|---|---|---|---|
| A. FEED | 0 | 0.00 | 358.95 | | 102.26 | | 24.22 | |
| B | 16 | 128.00 | 400.95 | 11.70% | 53.13 | -48.04% | 24.03 | -0.80% |
| C | 24 | 128.00 | 404.62 | 12.72% | 31.69 | -69.01% | 23.32 | -3.70% |
| D | 128 | 128.00 | 429.50 | 19.65% | 31.46 | -69.24% | 22.45 | -7.32% |
| E | 240 | 128.00 | 447.32 | 24.62% | 18.87 | -81.55% | 20.63 | -14.81% |
| F | 480 | 128.00 | 452.09 | 25.95% | 6.55 | -93.59% | 17.34 | -28.40% |

FIG. 33

CJ26 and CJ40 to Makeup Water (adding CJ40 first and then CJ26)

| Sample ID | CJ40 Conc. in Solution (PPM) | CJ126 Conc. in Solution (PPM) | Chloride Actual Conc. (ppm) | % Change From Initial Conc. in Chloride | Sulfate Actual Conc. (ppm) | % Change From Initial Conc. in Sulfate | Nitrate Actual Conc. (ppm) | % Change From Initial Conc. in Nitrate |
|---|---|---|---|---|---|---|---|---|
| A. FEED | 0 | 0.00 | 368.85 | | 107.33 | | 25.56 | |
| B | 16 | 128.00 | 411.95 | 11.68% | 57.80 | -46.15% | 24.83 | -2.85% |
| C | 24 | 128.00 | 410.03 | 11.16% | 35.89 | -66.56% | 25.16 | -1.58% |
| D | 128 | 128.00 | 426.66 | 15.67% | 29.41 | -72.60% | 24.00 | -6.12% |
| E | 240 | 128.00 | 465.15 | 26.11% | 22.24 | -79.28% | 25.47 | -0.34% |
| F | 480 | 128.00 | 501.62 | 36.00% | 8.50 | -92.08% | 19.33 | -24.37% |

FIG. 34

Various Captymers with CJ40 to Makeup Water

| Sample ID | CJ40 Conc. in Solution (PPM) | Captymer Conc. in Solution (PPM) | Chloride Actual Conc. (ppm) | % Change From Initial Conc. in Chloride | Sulfate Actual Conc. (ppm) | % Change From Initial Conc. in Sulfate | Nitrate Actual Conc. (ppm) | % Change From Initial Conc. in Nitrate |
|---|---|---|---|---|---|---|---|---|
| CJ14 feed | 0 | 0.00 | 359.05 | | 109.52 | | 24.33 | |
| A | 128 | 240.00 | 435.60 | 21.32% | 28.03 | -74.41% | 19.22 | -20.98% |
| B | 240 | 240.00 | 466.12 | 29.82% | 21.26 | -80.59% | 19.64 | -19.26% |
| C | 480 | 240.00 | 511.61 | 42.49% | 5.18 | -95.27% | 19.02 | -21.81% |
| CJ18 feed | 0 | 0.00 | 359.05 | | 109.52 | | 24.33 | |
| A | 128 | 240.00 | 460.79 | 28.33% | 19.75 | -81.97% | 19.73 | -18.88% |
| B | 240 | 240.00 | 478.83 | 33.36% | 14.70 | -86.58% | 17.99 | -26.05% |
| C | 480 | 240.00 | 525.40 | 46.33% | 4.54 | -95.86% | 17.47 | -28.18% |

US 8,658,702 B2

SOLUBLE ANION EXCHANGERS FROM HYPERBRANCHED MACROMOLECULES

CROSS-REFERENCE TO RELATED APPLICATION

The present application hereby claims priority of U.S. Provisional Patent Application Ser. No. 61/287,648, filed Dec. 17, 2009, entitled "Extraction of Anions from Water and Wastewater Using Functionalized Hyperbranched Macromolecules," which is incorporated herein by reference in its entirety.

GOVERNMENT RIGHTS

The United States Government has certain rights in this invention pursuant to CBET Grant No. 0506951 awarded by the National Science Foundation.

TECHNICAL FIELD

This subject matter relates generally to methods of and apparatuses for using branched macromolecules to extract anions such as bromide and nitrate from water, wastewater, and other aqueous solutions.

BACKGROUND

The availability of clean water has emerged as one of the most serious problems facing the global economy in the 21st century. See Savage, N. and Diallo, M. S. (2005) "Nanomaterials and Water Purification," *Journal of Nanoparticle Research,* 7(4-5): 331-42. Anions such as bromide, nitrate, and sulfate are major targets in water and wastewater treatment. Bromide ($Br^-$) is commonly found in surface water and groundwater. It can become a contaminant in drinking water when it is oxidized with ozone to bromate ($BrO_3^-$) during primary disinfection. The United States Environmental Protection Agency (USEPA) has identified bromate as a potential carcinogen and has established a maximum contaminant limit (MCL) of 0.01 mg/L in potable water. See 40 CFR 141.64(a). Because ozone does not generate a residual taste, color and odor in water, the multi-billion dollar U.S. bottled water industry uses ozonation to disinfect water prior to bottling and shipping. Removal of bromide from drinking water sources prior to ozonation is considered to be an effective means of satisfying the bromate MCL requirement.

Reverse osmosis (RO) is currently being used as the primary treatment process to remove bromide from water sources at most bottled water treatment plants. However, it is expensive to implement due the high pressure (e.g., roughly 10-70 bar) required to operate RO membranes. See *American Water Works Association, Reverse Osmosis and Nanofiltration* (M46), 2d ed., Denver, 2007. Moreover, two to three RO passes are often required to reduce bromide to acceptable levels prior to ozonation because of the limited bromide rejection capability of current RO membranes. Ion exchange (IX) is a widely used process for removing anions from water. See Gu, B. and Brown, G. M. (2006) "Recent advances in ion exchange for perchlorate, treatment, recovery and destruction," in *Perchlorate Environmental Occurrence, Interactions and Treatment*, Gu, B. and Coates, J. D., eds., Springer: New York, pp. 209-51. However, major drawbacks of IX include limited binding capacity/selectivity for bromide, and environmental impact (e.g., brine management and disposal). See id. Because of this, the bottled water industry is in critical needed for efficient, cost effective and environmentally acceptable technologies for removing bromide from drinking water sources prior to ozonation.

Nitrate ($NO_3^-$) is one of the most ubiquitous contaminants in groundwater, surface water and wastewater. It can reduce the ability of red blood cells to carry oxygen when ingested. The MCL of nitrate in drinking water is 45 mg/L. See Shannon, M. A., Bohn, P. W., Elimelech, M, et al. (2008), "Science and technology for water purification in the coming decades," *Nature,* 54: 301-10. Nitrate is often found in agricultural run-offs and municipal wastewater. The discharge of wastewater with excess nitrate in the Mississippi River has emerged as one of the main cause of hypoxia (i.e. oxygen deficiency) and the formation of the yearly "Dead Zone" in the Northern Gulf of Mexico (e.g., Louisiana and Texas). Nitrate removal from wastewater is a billion dollar industry in the US.

Biological processes (e.g., fluidized bed bioreactors, biological filters and membrane bioreactors) can effectively reduce nitrate to nitrogen ($N_2$) under anaerobic conditions. See Cheremisinoff, N. P. (2002) *Handbook of Water and Wastewater Treatment Technologies*, Butterworth-Heinemann: Boston. However, they are very sensitive to temperature changes. For example, a 10° C. decrease in temperature can cause up to a 50% reduction in biological denitrification activity. See Reynolds, T. D. & Richards, P. A. (1996) *Unit Operations and processes in Environmental Engineering,* 2d ed., PWS Publishing: Boston. Because of this, most wastewater treatment plants in the US cannot meet their nitrate discharge limit during the winter.

Excess sulfate is also considered harmful in drinking water. It may cause diarrhea in adults and infants when exposed suddenly to high levels of sulfate. (See Chien, L et al. (1968), "Infantile gastroenteritis due to water with high sulfate content," *Can Med Assoc J.* 99:102-104.

One approach to removing various contaminants from water is to use water-soluble branched macromolecules that selectively encapsulate dissolved solutes in aqueous solutions followed by ultrafiltration. See, e.g., U.S. Patent App. No. 2006/0021938 A1 (published Feb. 2, 2006); U.S. patent application Ser. No. 12/124,952; Diallo, M. S., Chritie, S., Swaminathan, P., Johnson, J. H. Jr., and Goddard W. A. III (2005) "Dendrimer Enhanced Ultrafiltration. 1. Recovery of Cu(II) from Aqueous Solutions Using Gx-$NH_2$ PAMAM Dendrimers with Ethylene Diamine Core," *Environmental Science and Technology,* 39(5): 1366-77; Diallo, M. S., Chritie, S., Swaminathan, P., Balogh, L., Shi, X., Um, W., Papelis, L, Goddard, W. A. III, and Johnson, J. H. Jr. (2004) "Dendritic Chelating Agents 1. Cu(II) Binding to Ethylene Diamine Core Poly(amidoamine) Dendrimers in Aqueous Solutions," *Langmuir* 20(7): 2640-51; Diallo, M. S., Wondwossen, A., Johnson, J. H. Jr., and Goddard, W. A. III (2008) "Dendritic Chelating Agents 2. U(VI) Binding to Poly(amidoamine) and Poly(propyleneimine) Dendrimers in Aqueous Solutions," *Environmental Science and Technology,* 42: 1572-79; and Diallo, M. S., Falconer, K., Johnson, J. H. Jr. and Goddard, W. A. Jr. (2007) "Dendritic Anion Hosts: Perchlorate Binding to G5-$NH_2$ Poly(propyleneimine) Dendrimer in Aqueous Solutions," *Environmental Science and Technology,* 41: 6521-27. See also U.S. Patent App. No. 2010/0181257 A1 (published Jul. 22, 2010), which is incorporated herein in its entirety.

There is a need, however, to develop effective novel macromolecules that enable anions such as bromide, nitrate, and sulfate removal technologies that are efficient, cost effective, and readily implemented using existing water or wastewater treatment equipment and infrastructure.

BRIEF SUMMARY

The present disclosure relates to the creation and use of novel macromolecules and supramolecular assemblies for filtering contaminants from water and non-aqueous solutions. Various embodiments are possible, a number of which are exemplified here.

The present disclosure describes a compound with the formula:

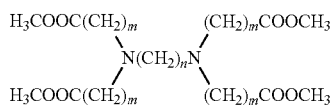

(Eq. 1)

wherein m and n may be integers from 2 to 5. Further described is a method of creating the compound of Eq. 1 by reacting methyl but-3-enoate with ethane-1,2-diamine, and then removing the side-product methanol.

Also described is a macromolecule with the formula:

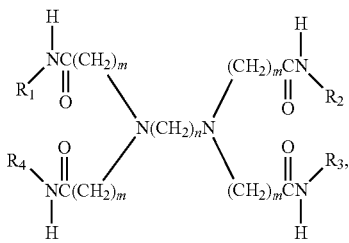

(Eq. 2)

where m and n may be integers from 2 to 5, and $R_1$-$R_4$ may be hyperbranched polymer moieties including, without limitation, polyethyleneimine (PEI) and various derivatives. Further described are methods Also described are methods for creating macromolecules of the formula Eq. 2 by reacting the compound of Eq. 1 with four hyperbranched polyethyleneimine (PEI) polymers. This cross-linked macromolecule can be further reacted with agents including without limitation paraformaldehyde, ethylene oxide, propylene oxide, and 1,2-epoxybutane to create functionalized macromolecules. Any of the above cross-linked macromolecules can be quaternized by, for example, reacting with a haloalkane or other suitable halo compound such as, without limitation, chloromethane, or for example with a dialkyl sulfate such as dimethyl sulfate.

Also described is a macromolecule with the formula:

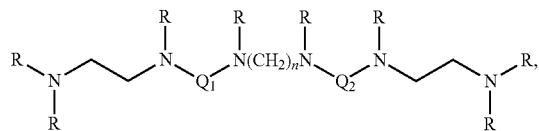

(Eq. 3)

where m might be from 2 to 5, or preferably 3, each of $Q_1$ and $Q_2$ can be a moiety comprising a hyperbranched polymer structure, and R can be a substituent such as hydrogen, an alkyl group, or a 2-hydroxyalkyl group. These macromolecules may be quaternized in a similar way to the macromolecules of Eq. 2.

Also described are filtration methods for removing contaminants (such as, without limitation, bromine, nitrate, and sulfate) from water or other aqueous solutions, including wastewater. In one embodiment, the aqueous solution is placed in contact with a cross-linked hyperbranched macromolecule, so that the macromolecule binds with the contaminant. The contaminant-bound macromolecule is then separated from the aqueous solution by means such as, without limitation, ultrafiltration, microfiltration, flocculation, or binding to a solid support such as a bead. Optionally, the contaminant-bound macromolecules can be placed in an environment where they dissociate, and the macromolecules may be recovered and optionally recycled.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings:

FIG. 21, FIG. 22, FIG. 23, FIG. 24, and FIG. 25, show examples of data illustrating the gradual removal of sulfate and nitrate as the amount of hyperbranched macromolecules CJ14, CJ18, CJ20, CJ26, and CJ28 respectively, are gradually added to makeup water at pH 7.1.

FIG. 26, FIG. 27, FIG. 28, and FIG. 29 show examples of data illustrating the gradual removal of sulfate and nitrate as both AN-5 and CJ14, CJ18, CJ20, and CJ26 are added to makeup water at pH 7.1.

FIG. 30 shows an example of data illustrating the gradual removal of sulfate and nitrate as the amount of CJ40 is gradually added to makeup water.

FIG. 31, FIG. 32, FIG. 33 show examples of data illustrating the gradual removal of sulfate and nitrate as both CJ40 and CJ14, CJ26, and CJ26, respectively, are added to makeup water.

FIG. 34 shows examples of data illustrating the gradual removal of sulfate and nitrate as both CJ40 and CJ14 and CJ18, respectively, are added to makeup water.

DETAILED DESCRIPTION

Various example embodiments of the present inventions are described herein in the context of filtering or separating aqueous solutions.

Those of ordinary skill in the art will understand that the following detailed description is illustrative only and is not intended to be in any way limiting. Other embodiments of the present inventions will readily suggest themselves to such skilled persons having the benefit of this disclosure, in light of what is known in the relevant arts, the provision and operation of information systems for such use, and other related areas. Reference will now be made in detail to exemplary implementations of the present inventions as illustrated in the accompanying drawings.

In the interest of clarity, not all of the routine features of the exemplary implementations described herein are shown and described. It will of course, be appreciated that in the development of any such actual implementation, numerous implementation-specific decisions must be made in order to achieve the specific goals of the developer, such as compliance with regulatory, safety, social, and business-related constraints, and that these specific goals will vary from one implementation to another and from one developer to another. Moreover, it will be appreciated that such a developmental effort might be complex and time-consuming, but would nevertheless be a routine undertaking of engineering for those of ordinary skill in the art having the benefit of this disclosure.

Figure 7:
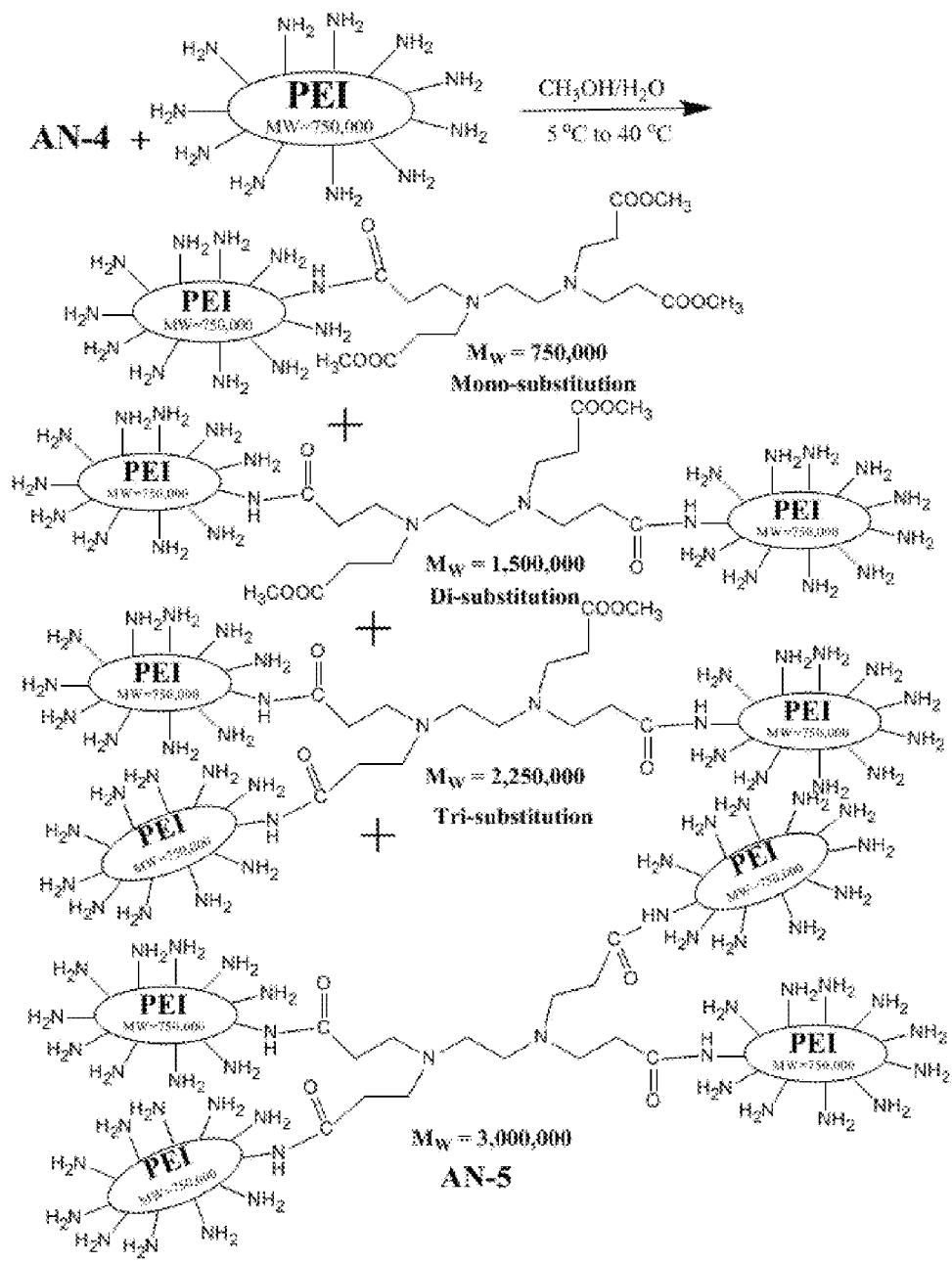
FIG. 7 shows a chemical reaction for cross-linking PEI (molecular weight roughly 750,000 Daltons) to ultimately produce a hyperbranched macromolecule with molecular weight of roughly 3 million Daltons, referred to herein as AN-5.

Throughout the present disclosure, relevant terms are to be understood consistently with their typical meanings established in the relevant art. However, without limiting the scope of the present disclosure, further clarifications and descriptions are provided for relevant terms and concepts as set forth below:

The terms hyperbranched polymer and hyperbranched as used herein refer to their definitions as known to those of skill in the art. A hyperbranched polymer comprises generally polydisperse branched macromolecules which are preferably prepared in a single synthetic polymerization step that forms imperfect branches, generally in a non-deterministic way. However, there are many preferable synthetic strategies known in the art to prepare hyperbranched polymers with lower polydispersity. They are typically characterized by their degree of branching (DB). An amine-based hyperbranched polymer may comprise tertiary, secondary, and primary amines, unless it has been modified, in which case the primary amines might as an example be converted to secondary and/or tertiary amines and secondary amines might, for example, be converted to tertiary amines, leading the same imperfect branched structure. A hyperbranched polymer structure may be part of a chemical moiety which may be attached to other moieties by means known to those of skill in the art, including without limitation attachment via an amide bond. A non-limiting example of such an attachment is shown in FIG. 7, wherein four hyperbranched polymer polyethyleneimine (PEI) moieties are attached via amide linkages to a central moiety derived from reagent AN-4.

The term degree of branching (DB) has a meaning known in the field of branched macromolecules, and use herein is consistent with that meaning A preferable definition is provided, for example, in C. J. Hawker, R. Lee, and J. M. J. Fréchet (1991), "The One-Step Synthesis of Hyperbranched Dendritic Polyesters," *J. Am. Chem. Soc.*, 113: 4583, which is incorporated herein by reference in its entirety.

The size of the polymers described herein may be measured by standard measurements of the average molecular weight, as is known by those of skill in the art. The molecular weight may be a number average molecular weight, $M_n$, or a weight average molecular weight, $M_w$. The distribution of the molecular weight of specific compounds of the polymers may be reflected in the ratio of the weight average molecular weight over the number average molecular weight ($M_w/M_n$). Those of skill in the art call this ratio the polydispersity index or polydispersity of the polymer.

Figure 1:
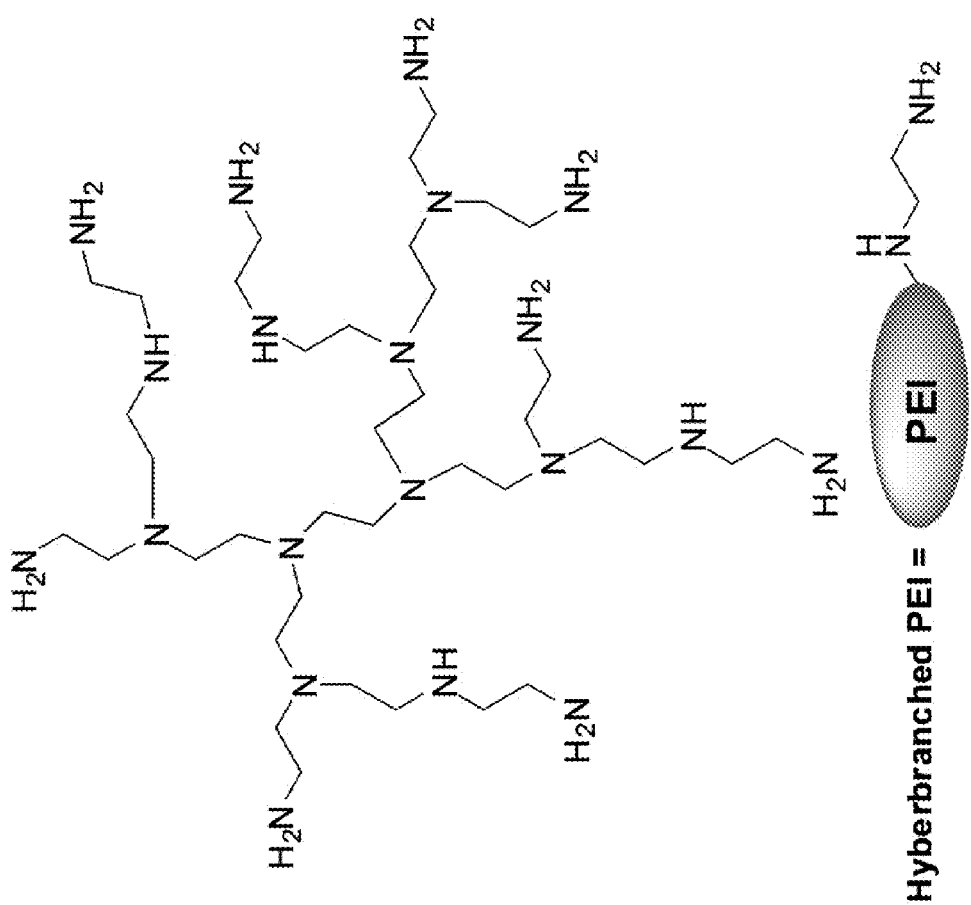
FIG. 1 shows an example of a hyperbranched poly(ethyleneimine) polymer as a building block for some of the hyperbranched macromolecules described in this disclosure. PEI may also exist in other configurations, as known in the art and as described herein.

The term hyperbranched polyethyleneimine (PEI) polymer or PEI refers to a class of hyperbranched polymers known in the art. An example of a PEI molecule is shown in FIG. 1, but many others are known in the art. One way to describe PEI is by the formula —$(CH_2$—$CH_2$—$NH)_n$—, where n is from about 10 to at least $10^5$. Generally, PEI polymers have a degree of branching (DB) of approximately 65-70%, consisting of primary, secondary, and tertiary amines, the amines being linking by $C_2$ alkyl chains. PEI with various molecular weights (MW) ranging from about 1,000 to several million Daltons are commercially available. A bulk PEI composition for use in this disclosure preferably have an average $M_w$ of about 750 KDa and a polydispersity index of about 12.5. However, PEI with $M_w$ of greater than about 750 KDa (for example, ranges including 1 or 2 MDa) or with a polydispersity index of lower than 12.5 (for example, polydispersity ranges including 10, 7.5, 5, 2.5 or lower) is even more preferable, though likely to be more expensive. Similarly, a $M_w$ much lower than 750 kDA (for example, ranges extending as low as 500, 250, 50, 25, 1.5 kDa, or lower), or with a polydispersity index greater than 12.5 (for example, ranges extending as high as 13, 15, 20 or higher), may also have the advantage that they are less expensive, but are less preferred from an efficiency standpoint because larger molecules can be more easily filtered by ultrafiltration, microfiltration, or other similar membrane means. Among many ways known in the art for preparing PEI, one preferable and non-limiting example is through one step synthesis by ring opening polymerization of aziridine, also known as ethylene imine.

The term extent of binding (EOB) has its normal meaning in the field, and refers to the number of moles or grams of bound ions per mole or gram of macromolecule. It is used to quantify the uptake of anion contaminant by branched macromolecules in aqueous solutions. If the macromolecule is very large, polydisperse, or highly cross-linked, it is more convenient to express the EOB on a mass basis. In FIG. 14 to FIG. 18 of this disclosure, binding data are fitted to the Langmuir model given below:

$$EOB = \frac{C_{max}K[APL]}{1.0 + K[APL]} \quad \text{Eq. 1}$$

where EOB (mg/g) is the extent of binding, where $C_{max}$ is the binding capacity (mg/g), K is an "operational" binding constant, and APL (mg/g) is the anion-polymer loading (mg/g).

The term moiety as used herein refers to any part of an organic molecule, and may include, without limitation, a functional group, an alkyl chain, a branch of a branched molecule, or a continuation of a branched structure.

Branched macromolecules are a versatile class of nanomaterials, and can be engineered to selectively bind to, or react with, a particular element, ion, or molecule. Such molecules may include hyperbranched polymers, or various other branched configurations. Some of them are soluble in aqueous solutions, while others are insoluble. They may exist in a variety of sizes and shapes, and may be designed to have hundreds or even thousands of complexing sites and reactive chain-ends. They can be covalently linked to each other or to other macromolecules to form supramolecular assemblies of various size, shape and topologies.

Figure 20:
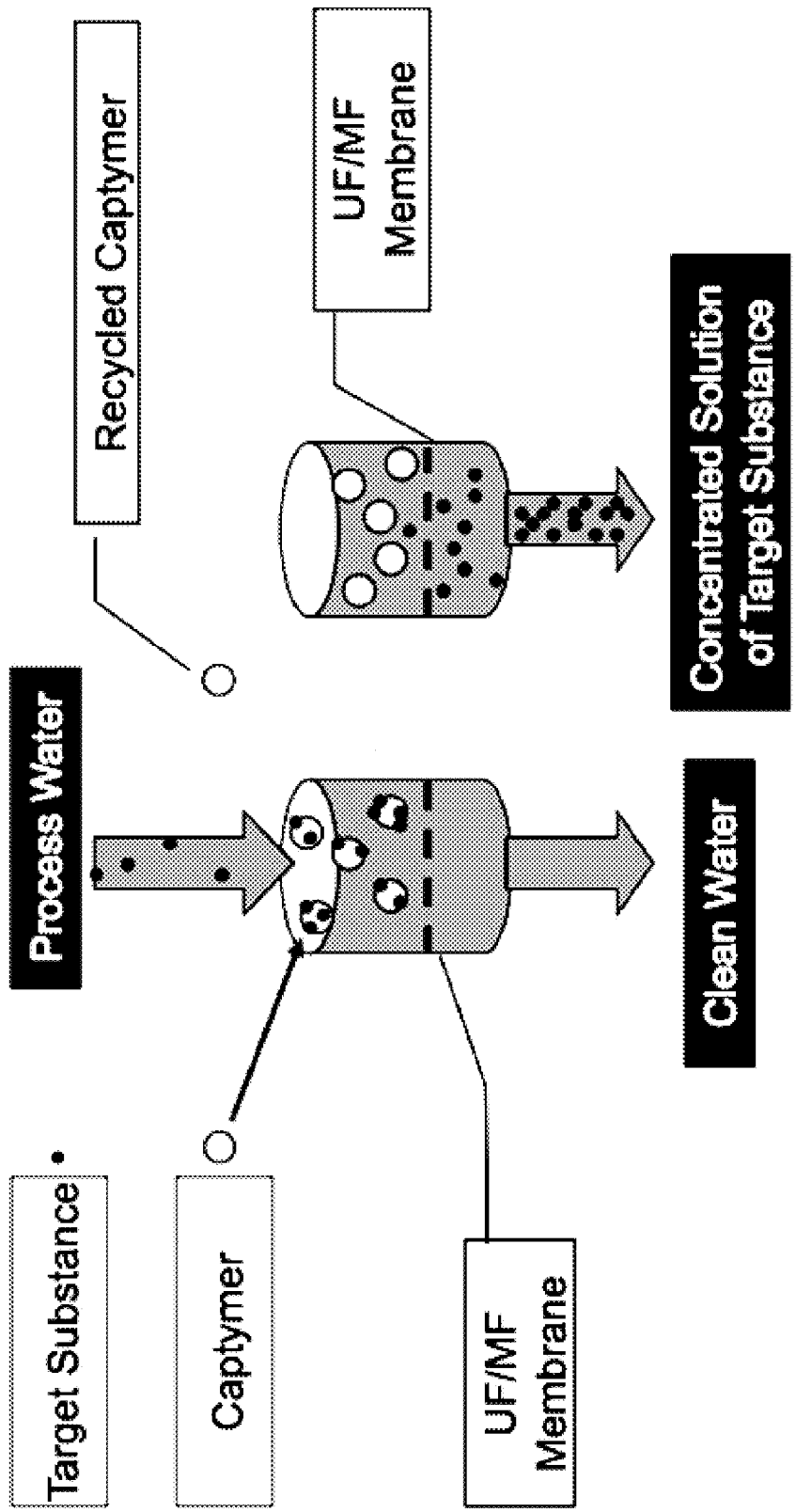
FIG. 20 shows an example of a water treatment process using hyperbranched macromolecules (referred to as "captymers") and ultrafiltration or microfiltration.

Branched macromolecules can be used in a number of ways to filter or separate ions in aqueous solution. For example, dendrimer-enhanced filtration (DEF) may be used, using a two-step filtration process described in U.S. Pat. No. 7,470,369 (FIG. 1 thereof, and related text), which is incorporated herein in its entirety. In this particular design, water may be mixed in a Treatment Unit with water-soluble dendritic macromolecules that bind the target contaminant molecules (in this example anions) at a particular chemical environment (in this case low pH of around 4-5). The complexes of macromolecules and bound anions may then be filtered using ultrafiltration (UF), microfiltration (MF), or equivalent technologies. The resulting concentrated solution of macromolecules and bound contaminant molecules may subsequently be sent to a Recovery Unit. This system may consist of an UF/MF unit in which the bound target anions may be released by changing the chemical environment (in this example, increasing the solution pH to around 9-10). Finally, the recovered concentrated solution of target substance may be collected for disposal or subsequent processing while the macromolecules may be recycled. For an illustrative example, see FIG. 20.

This disclosure describes technologies for water filtration that can be integrated into existing water or wastewater treatment plants in at least the following two ways. First, a non-recyclable anion selective macromolecule may be added to water or wastewater, and then removed by any macromolecule removal process known in the art such as, without limitation, flocculation with settling, media or membrane filtration technology. Second, a recyclable anion selective macromolecule may be added to water or wastewater, and then separated using any suitable separation process known in the art, including without limitation ultrafiltration or microfiltration.

The design of selective hosts for anions, in particular, is a very challenging undertaking. Unlike cations, anions have filled orbitals and thus cannot covalently bind to ligands in most cases. The interactions of anions with supermolecular hosts depend on various factors including: (i) electrostatic interactions, (ii) hydrophobic interactions, (iii) hydrogen bonding, (iv) Van del Waals interactions, (v) solution pH and ionic strength, (vi) solvent polarity, (vii) host shape and (viii) guest size. The physiochemical properties of several common anions in water purification and wastewater treatment are listed in Table 1, including ionic radius in nm, hydration free energy in KJ/mol, charge-to-radius ratio and shape. Note that among these anions, perchlorate ($ClO_4^-$) has the highest hydration free energy (−205 KJ/mol), i.e. the most difficult to be hydrated; and sulfate ($SO_4^{2-}$) has the lowest hydration free energy (−1080 KJ/mol), i.e. the easiest to be hydrated. Nitrate ($NO_3^-$) and bromide (Br), both monovalent anions, though with different shapes, have comparable hydration free energies; −300 KJ/mol vs −315 KJ/mol. Thus, one may exploit the difference between the hydration free energies of the target anions to tune their binding affinity toward supramolecular hosts with differing hydrophobicity and polarity.

TABLE 1

Physicochemical properties of selected anions of interest to water and wastewater treatment.
Data are taken from Gloe, K.; Stephan, H. and Grotjahn, M. (2003), "Where is the anion extraction going? *Chem. Eng. Technol.* 26: 1107-1117.

| Anion | Ionic Radius (nm) | Hydration Free Energy (KJ/mol) | Charge-to-Radius Ratio | Shape |
|---|---|---|---|---|
| $Cl^-$ | 0.172 | −340 | 5.81 | Spherical |
| $Br^-$ | 0.188 | −315 | 5.32 | Spherical |
| $NO_3^-$ | 0.196 | −300 | 5.10 | Trigonal Planar |
| $ClO_4^-$ | 0.240 | −205 | 4.17 | Tetragonal |
| $H_2PO_4^-$ | 0.200 | −465 | 5.00 | Tetragonal |
| $SO_4^{2-}$ | 0.230 | −1080 | 8.69 | Tetragonal |

Figure 2:
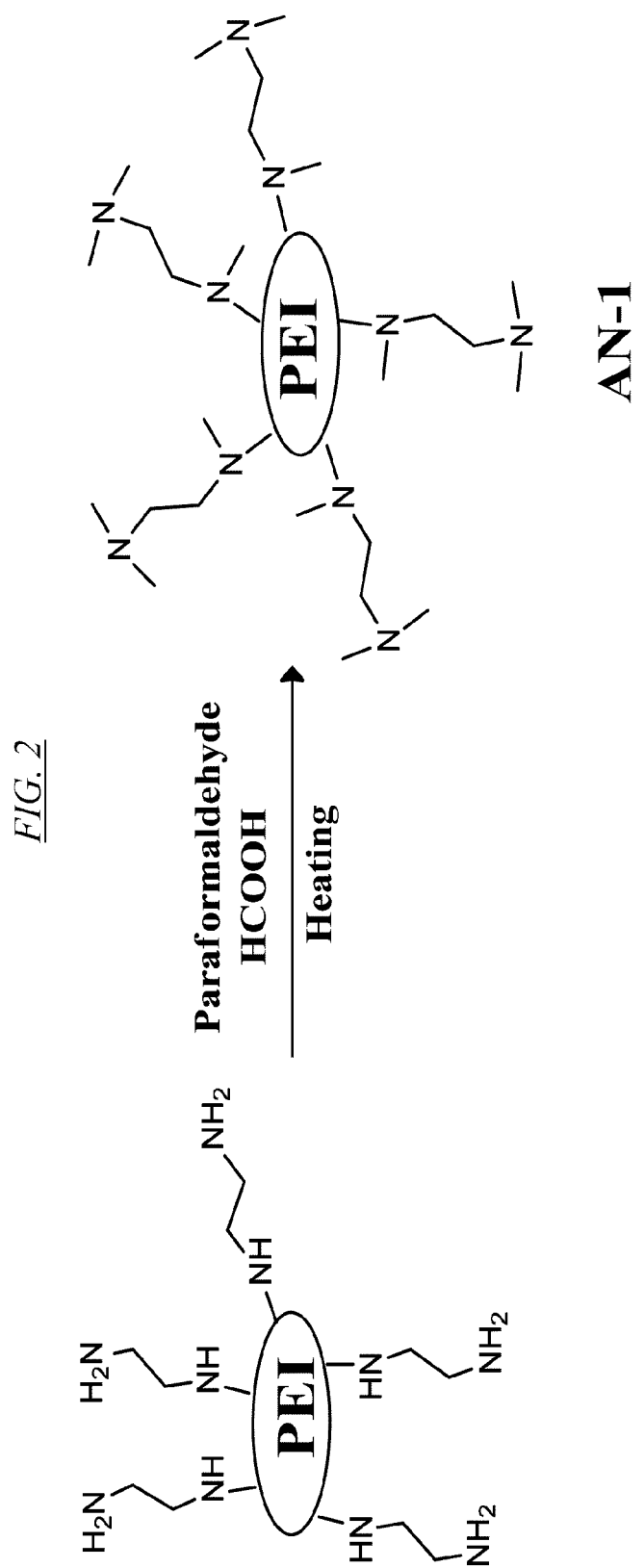
FIG. 2 shows a chemical reaction for synthesis from PEI of a hyperbranched macromolecule, referred to herein as AN-1.
Figure 3:
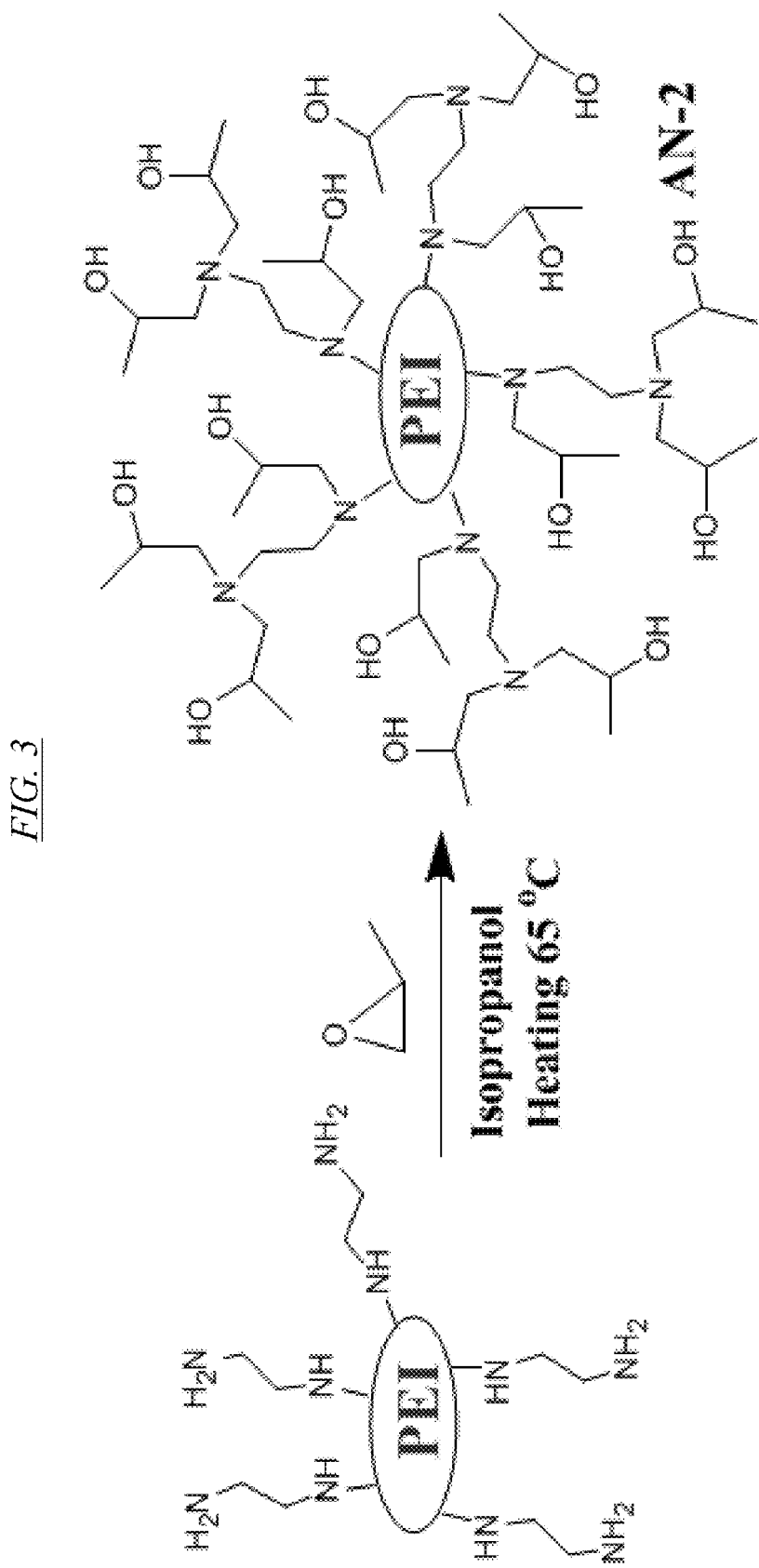
FIG. 3 shows a chemical reaction for synthesis of a hyperbranched macromolecule, referred to herein as AN-2.
Figure 4:
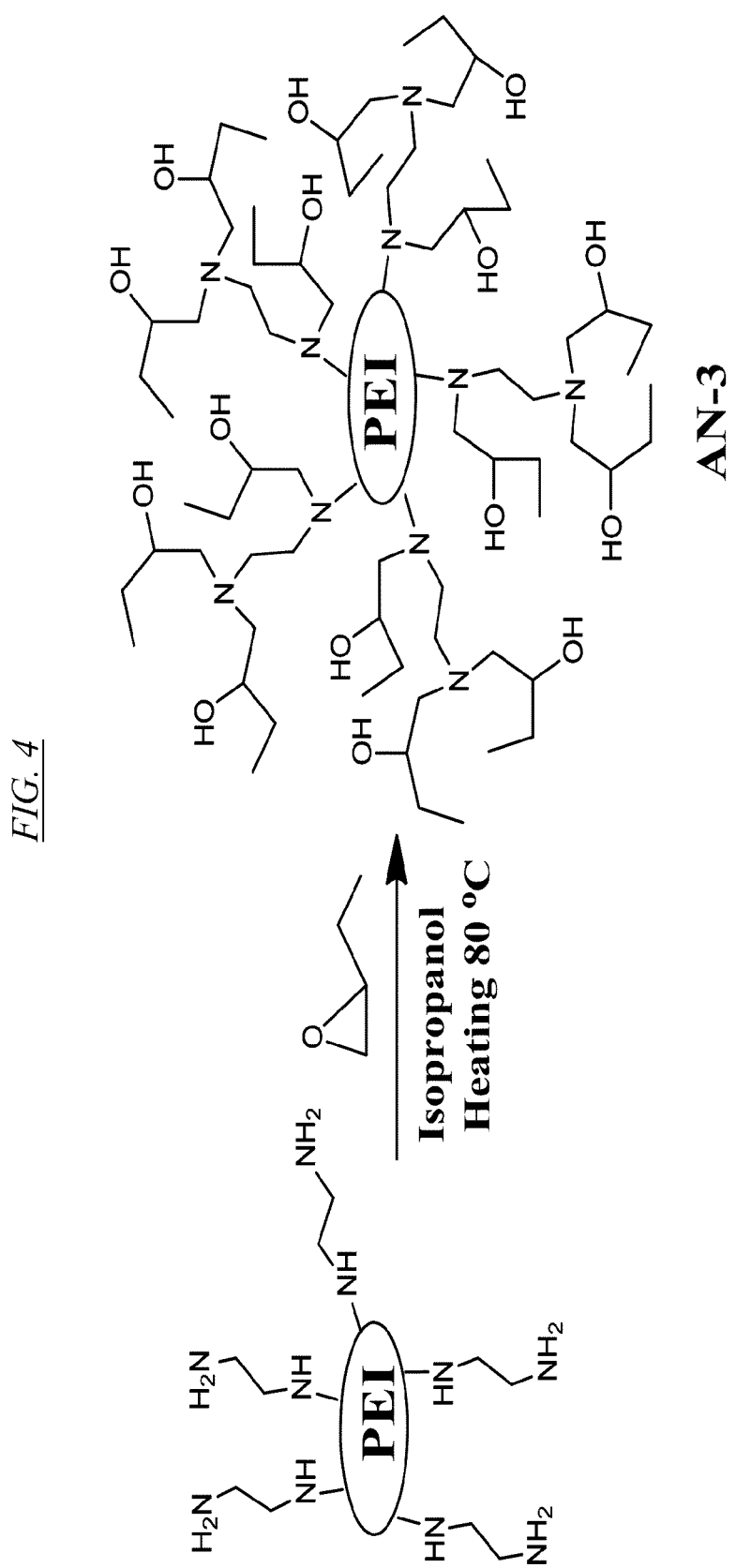
FIG. 4 shows a chemical reaction for synthesis of a hyperbranched macromolecule, referred to herein as AN-3.

Replacement of the protons on the primary and secondary amines of PEI by reactive functional groups of differing hydrophobicity can be used to prepare recyclable anion-selective supramolecular hosts with very large binding capacity. For example, FIG. 2 shows a chemical reaction for synthesis from PEI of a hyperbranched macromolecule, referred to herein as AN-1. FIG. 3 shows a chemical reaction for synthesis of a hyperbranched macromolecule, referred to herein as AN-2. FIG. 4 shows a chemical reaction for synthesis of a hyperbranched macromolecule, referred to herein as AN-3. In each of these three cases, a proton is replaced with an N-substituent to produce a functionalized hyperbranched macromolecule in which substantially all of the original primary and secondary amine linkages have been converted to tertiary amine linkages.

Figure 5:
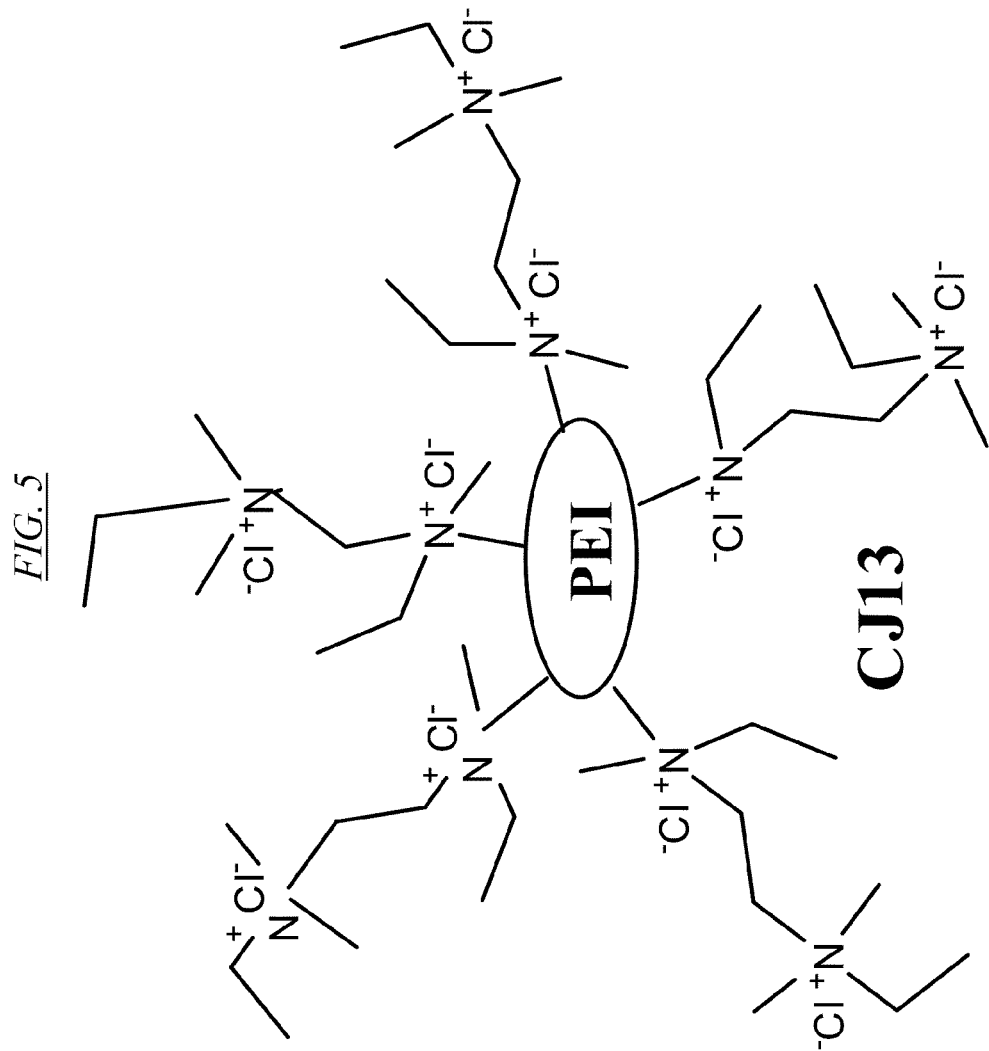
FIG. 5 shows an example of a hyperbranched macromolecule with quaternary amines, referred to herein as CJ13.

FIG. 5 shows an example of a hyperbranched macromolecule (CJ13) which has been converted into a quaternary structure. Thus, a second N-substituent is added to each of the amine nitrogen atoms, converting the molecule into a polar molecule. There are many effective choices for this second N-substituent, which is preferably a primary haloalkane, and most preferably chloromethane.

To produce commercially viable branched macromolecules, it is useful, but not necessary, to provide macromolecules such as PEI having a very large molar mass, which will assist in their separation from aqueous solutions using commercially available hollow fiber UF membranes with relatively large pore size. Preferably but not necessarily, the molecular weight will be at least 150 KDalton. Also, it is useful, but not necessary, for commercial purification of nitrates in wastewater that the macromolecules in use are not pH sensitive, given that a typical pH of wastewater may be between roughly 6.5 and 8.5. Such non-pH sensitive macromolecules may in some instances not be recyclable, if the normal means of recovery and recycling is to place them in a high-pH environment and separate the bound ligands from the unbound macromolecules, since the wastewater is already at a relatively high pH.

Thus, using the information presented in this disclosure, one may for example, and without limitation, selectively remove bromide from drinking water sources prior to ozonation, or selectively remove excess nitrate from wastewater prior to discharge in receiving surface water bodies. One of skill in the art will understand that because bromide and nitrate have similar physicochemical properties, the utility of macromolecules in binding with nitrate strongly implies usefulness with regard to bromide, and vice versa.

It is useful to synthesize, and use for water or wastewater filtration, high molecular weight PEI or PEI-based macromolecules, which may be used for water or wastewater filtration using relatively large pore filters or other separation means that separate molecules on the basis of size or molecular mass. Such larger macromolecules may enhance anion binding capacity and also may enable the use of low-pressure hollow-fibers UF membranes with relatively large pore size.

Figure 6:
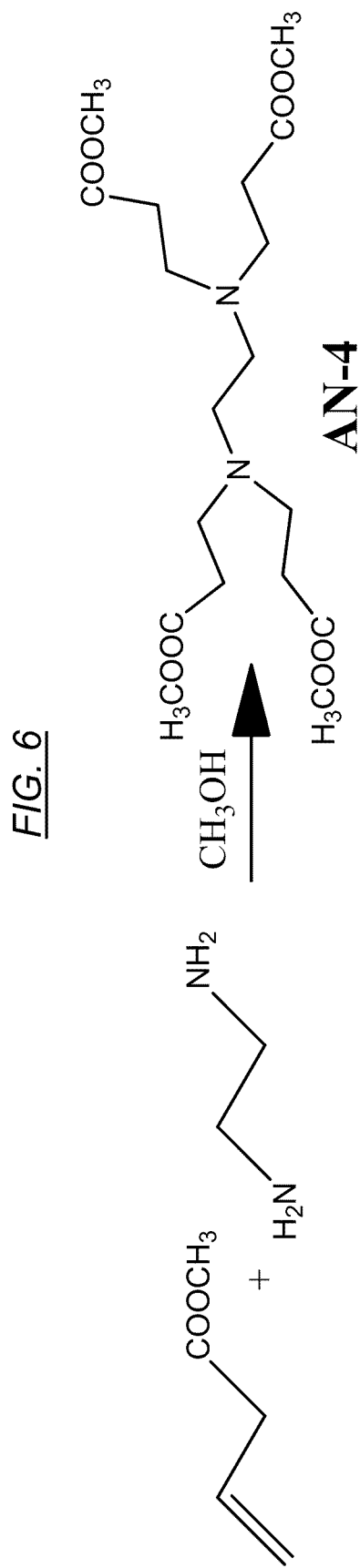
FIG. 6 shows a chemical reaction for synthesizing a cross-linking reagent, referred to herein as AN-4, or tetramethyl 3,3',3'',3'''-(ethane-1,2-diylbis(azanetriyl))tetrapropanoate.

One method of preparing such high molecular weight PEI macromolecules is through targeted cross-linking to synthesize high molecular weight and preferably water-soluble PEI macromolecules for subsequent functionalization. For example, FIG. 6 describes a reaction for synthesis of a relatively inexpensive cross-linking reagent referred to herein as AN-4. Other suitable cross-linking reagents may include 1,3-diiodopropane or other primary diiodoalkanes.

As an illustrative example for synthesizing AN-4, 70 g of methyl acrylate and 80 mL of methanol may be added to a 500 mL flask; while the solution is cooled into an ice-water bath, a solution of 10 g of ethylene diamine in 80 mL of methanol may be added dropwise within 2 h under magnetic stirring. The resulting solution may be stirred at the same temperature for additional two hours and warmed up to room temperature and stirred overnight. Solvent may be removed and the mixture may be further co-evaporated with ethyl acetate to give the crosslinking reagent AN-4.

FIG. 7 illustrates a preferable cross-linking reaction of PEI, during which there are stepwise reactions leading to the formation of a branched macromolecule referred to herein as AN-5 and CJ30, which has a preferred weight average molecular weight of at least about 3.0 million Daltons, though the molecular weight can be much lower. A significant issue in choosing the macromolecule size is to balance the cost of the larger molecules, against the cost of filtering or separating the macromolecules from the solution using smaller molecules.

During the synthesis of AN-5, four methyl esters are gradually and slowly replaced by only primary amines of PEI to form strong amide bonds, which may avoid the formation of polymer gels. Methanol ($CH_3OH$) is a side product of this reaction, but it can easily be removed by means known to one of skill in the art, which may require no further purification. As an illustrative example, AN-5 may be synthesized as follows: to 30 g of 33% of PEI solution ($M_w$=750,000, net 10 g of PEI) in a 500 flask may be added 100 mL of methanol and resulting solution may be cooled into an ice water bath. With vigorous stirring, a solution of 24 mg (0.059 mmol) of AN-4 in 2 mL of methanol may be added slowly through a syringe. The resulting solution may be stirred at the same temperature for additional two hours and warmed up to room temperature and stirred overnight. The mixture may be dialyzed with 100 K cutoff membrane to remove small molecules and other impurities.

Due to large number of primary amine groups in PEI, unwanted intermolecular and intramolecular substitutions can have an effect. Table 2 shows the ratios of AN-4 to PEI in one illustrative embodiment. This table assumes for this example that the average molecular weight of the PEI as 750,000, and that the PEI has about 37% primary amines, 33% secondary amines, and 30% tertiary amines.

TABLE 2

Evaluation of Various Amount of Crosslinking Reagent (AN-4)

| PEI (g)* | AN-4 (mg) | AN-4:PEI Ratio | AN-4:Primary Amine Ratio |
|---|---|---|---|
| 10 | 2.0 | 1:2.68 | 1:15,353 |
| 10 | 3.0 | 1:1.80 | 1:10,270 |
| 10 | 24.0 | 1:0.22 | 1:1,288 |
| 10 | 48.0 | 1:0.12 | 1:704 |

In this example, the retention of the cross-linked PEI macromolecules (AN-5) by polyethersulfone (PES) UF membranes may be measured with molecular weight cut-off (MWCO) of 3000 and 150000 Daltons. Their binding capacities for nitrate and bromide (at pH 5 and 9.01) in deionized water and the low/high ionic strength makeup groundwater may also be measured as illustrated in this disclosure. Using the results of retention and binding experiments, one may determine the optimal cross-linking degree of the base PEI that may be obtained from a commercial or other source for subsequent functionalization.

Figure 8:
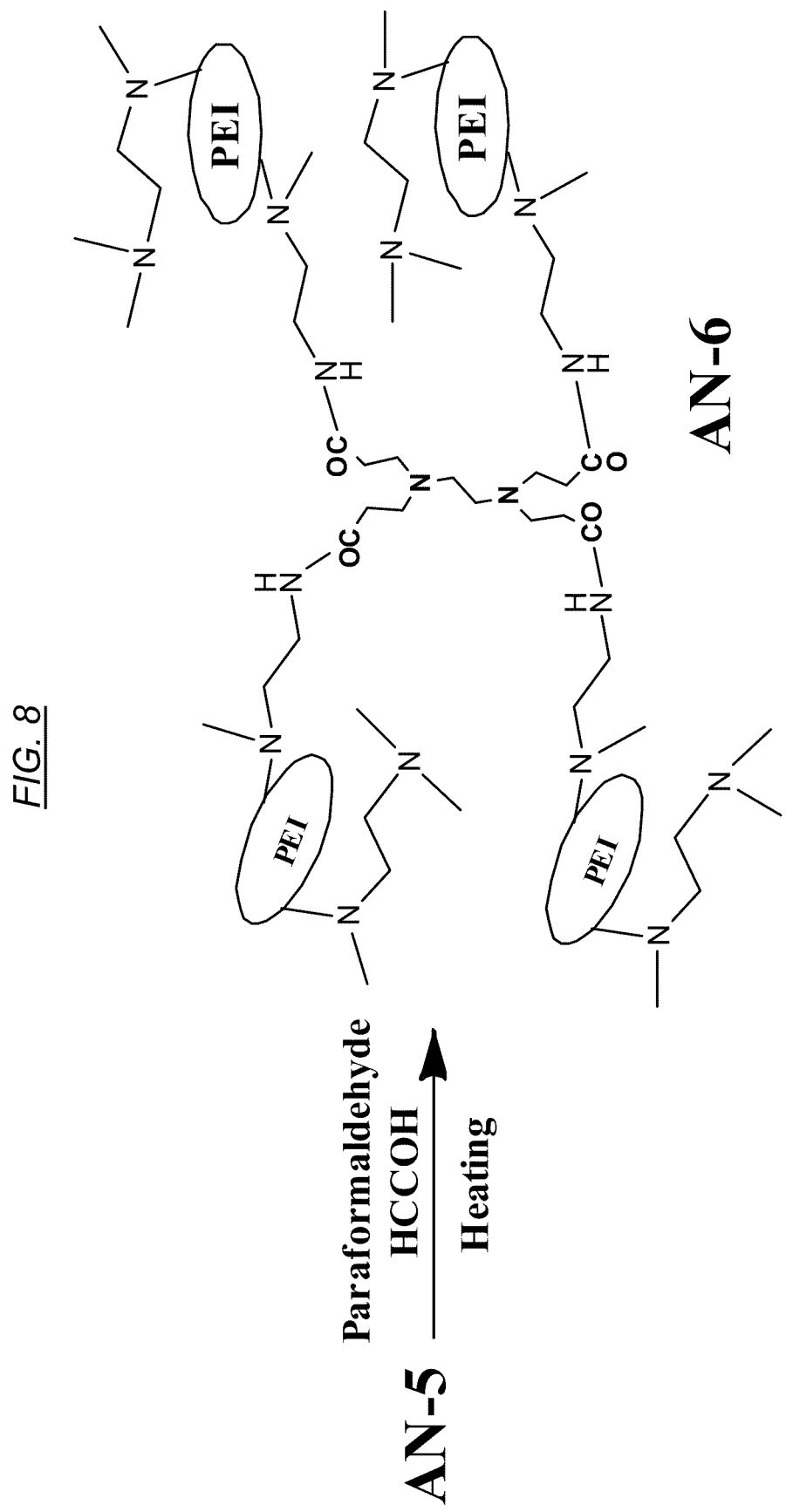
FIG. 8 shows a chemical reaction for synthesis from AN-5 of a recyclable, cross-linked, hyperbranched macromolecule, referred to herein as AN-6, CJ10, and CJ40.

In the illustrative embodiment described in FIG. 8, a functionalized macromolecule referred to as AN-6 (also called CJ10 or CJ40) may for example be synthesized by methylation of AN-5 with five equivalents of paraformaldehyde and 10 equivalents of formic acid. An illustrative example of preparing AN-6 is as follows: to 100 g of AN-5 in 2000 mL flask may be added 350 g of paraformaldehyde and 1.2 kg of formic acid, the mixture may be heated at 80.0 C for three days with occasional shaking Solvent may be removed using a high vacuum pump and the resulting gum type materials may be co-evaporated with 500 mL of toluene. Into this gum materials may be added 500 mL of water, and 184 g of NaOH may be added portion by portion (pH of the solution can be about 7.0). The crude product may be purified by dialysis using a 10 K cut-off membrane and the purified product may be concentrated to give polymer AN-6.

Figure 9:
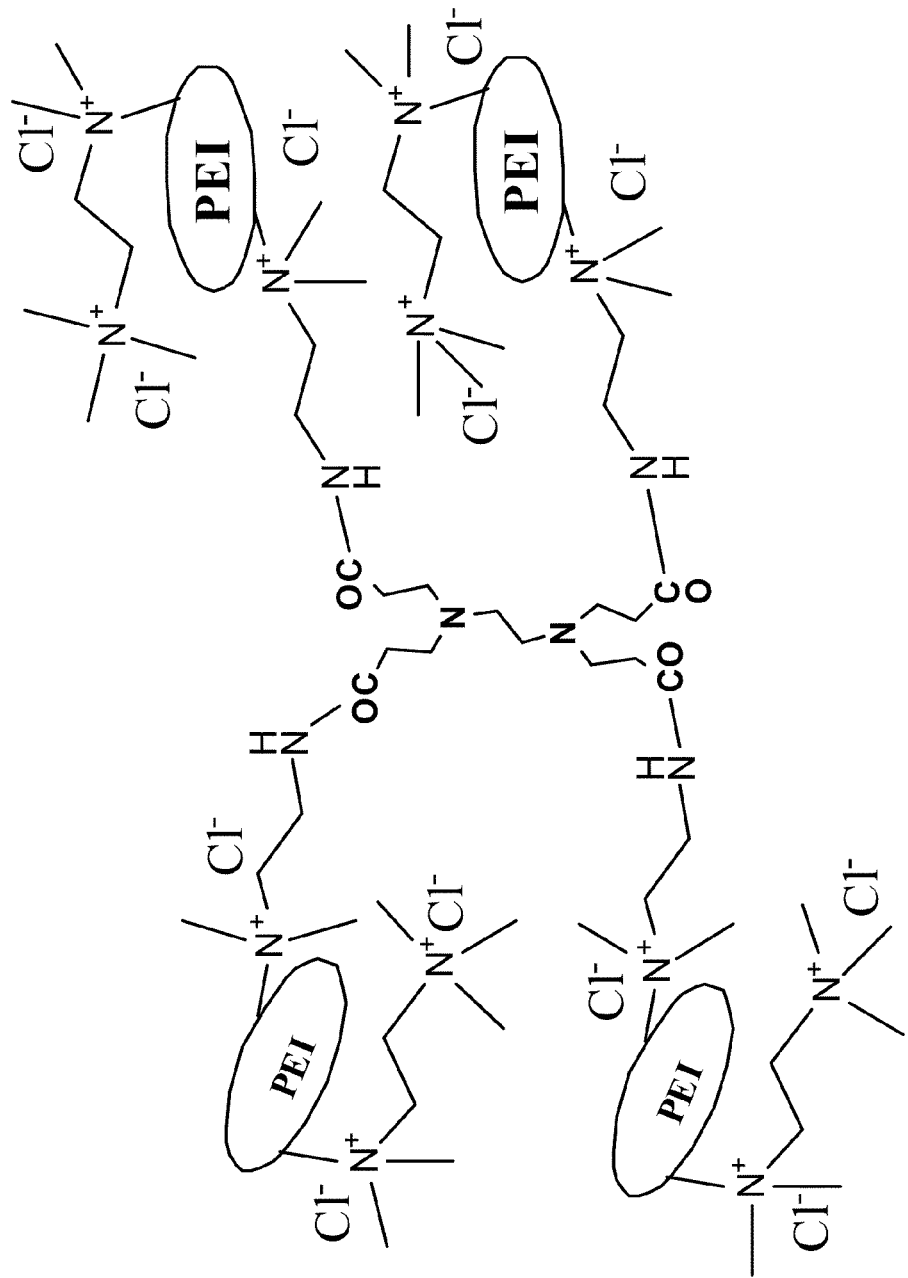
FIG. 9 shows a cross-linked hyperbranched macromolecule comprising quaternary amines, referred to herein as CJ18.
Figure 10:
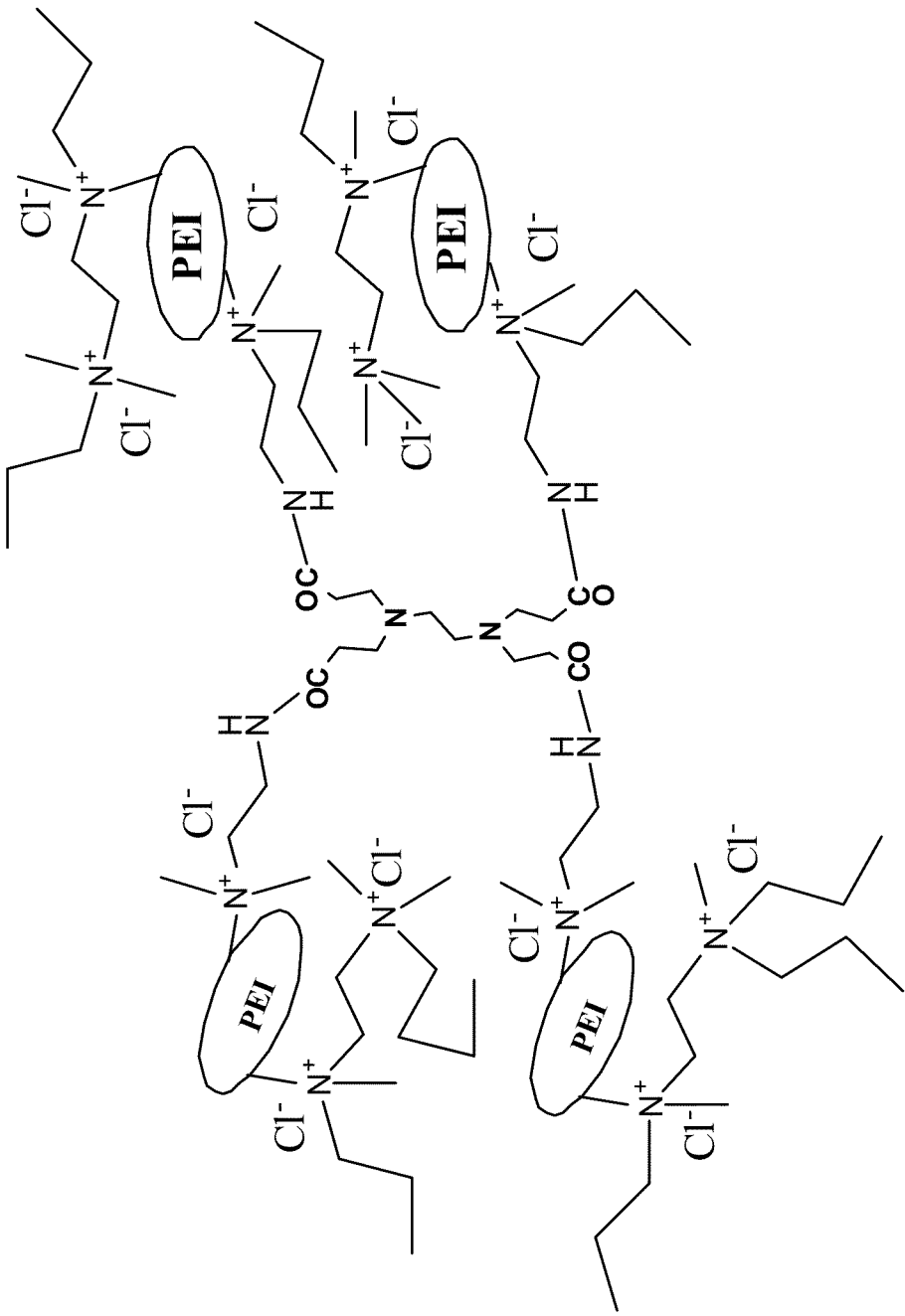
FIG. 10 shows a cross-linked hyperbranched macromolecule comprising quaternary amines, referred to herein as CJ14.

Another example compound may be formed by reacting AN-5 with 1,2-epoxybutane in the presence of isopropanol at approximately 65-80° C., preferably using a sealed pressure vessel. Both this compound and AN-6 may be quaternized in a manner similar to CJ13, as discussed above in relation to FIG. 5. The quaternized versions of these methyl- and epoxybutane-functionalized molecules are shown in FIG. 9 and FIG. 10, respectively.

When macromolecules are both functionalized with a first N-substituent and quaternized with a second N-substituent, functionalizing with the first N-substituent and then quaternizing with the second N-substituent may be equivalent to functionalizing with the second N-substituent and quaternizing with the first N-substituent.

An illustrative example of synthethizing the structure of FIG. 9 (referred to as CJ18) is as follows: to 9.8 gm of AN-6 (CJ10) may be added 60 mL of ethanol and 15 mL of dimethyl sulfate and the mixture may be heated to 75° C. for 10 min. The pH of the solution may be adjusted to higher than 9.0 by adding 3 N NaOH solution and heating again at the high temperature for another 10 min. The mixture may be cooled to room temperature and diluted by adding 2.0 L of 5% NaCl solution and purified by dialysis using either 10K or 100 K cutoff membrane. The purified material may then be concentrated to give CJ18.

An illustrative example of synthesizing the structure of FIG. 10 (referred to as CJ14) is as follows: to 8.0 g of AN-6 (CJ10) may be added 60 mL of ethanol and 40 mL of 3-chloropropane in a 250 mL pressure vessel and the mixture may be sealed and heated at 80° C. overnight. After cooling to room temperature, the solvents may be removed to give a powder material and the resulting material may be purified by dialysis using either 10K or 100 K cutoff membrane. The purified material may be concentrated to give CJ14.

Figure 12:
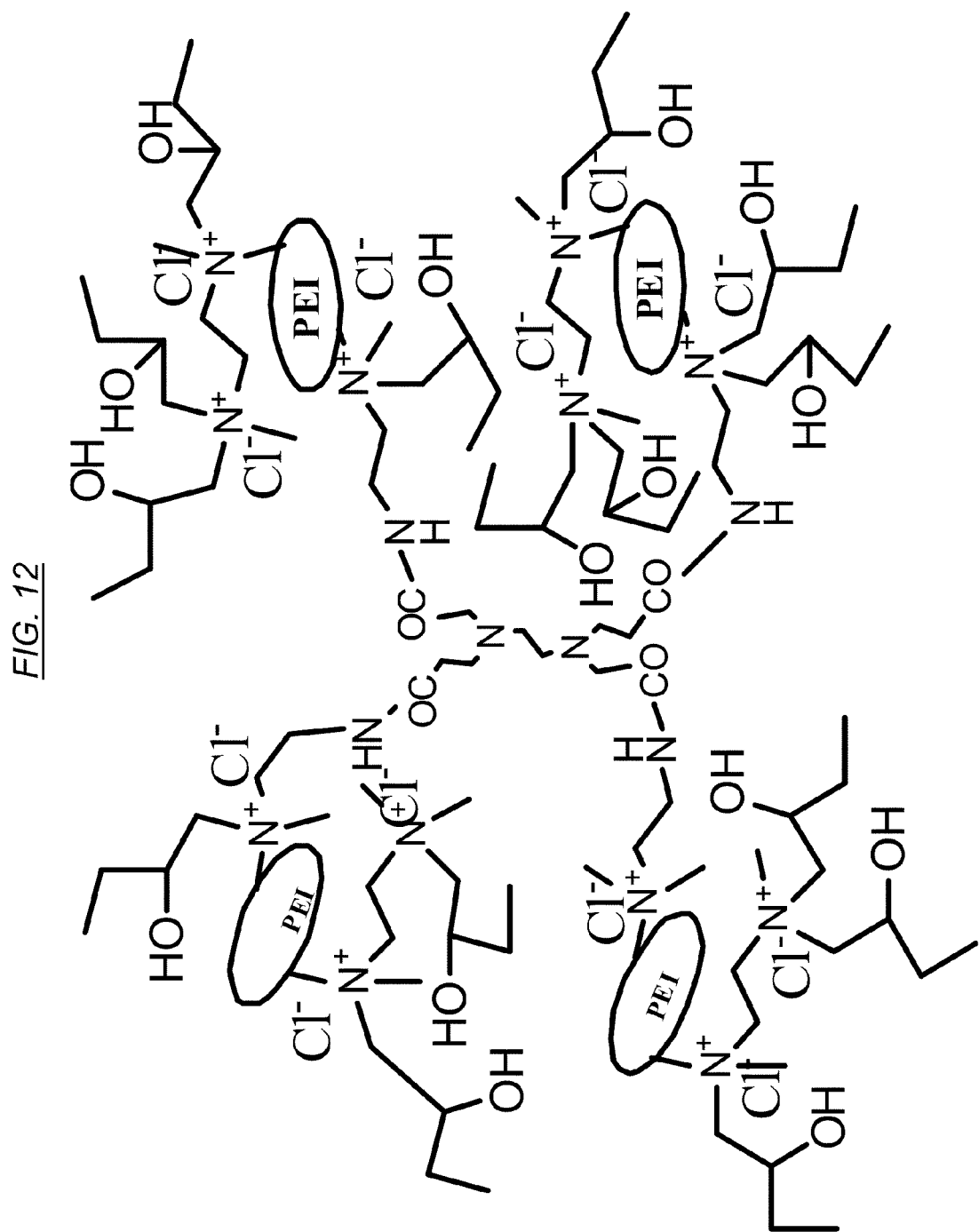
FIG. 12 shows a cross-linked hyperbranched macromolecule comprising quaternary amines, referred to herein as CJ20 and CJ26.

An illustrative example of synthesizing the structure of FIG. 12 (referred to as CJ20 and CJ26) is as follows: to 300 mL of pressure vessel may be added 20 g of AN-6 (CJ10), 50 mL of isopropanol, and 45 g of 1,2-epoxybutane. The cap may be sealed and heated at an oil bath with temperature at 80° C. for 4 days. After cooling to room temperature, the solvents may be removed through a rotavapor and co-evaporated with 100 mL of toluene. Into this mixture may be added 120 mL of ethanol and 45 mL of dimethyl sulfate and the mixture may be heated to 75° C. for 10 min. The pH of the solution may be adjusted to hither than 9.0 by adding 3 N NaOH solution and heating again at the high temperature for another 10 min. The mixture may be cooled to room temperature and diluted by adding 2.5 L of 5% NaCl solution and purified by dialysis using either 10K or 100 K cutoff membrane. The purified material may be concentrated to give CJ20.

Figure 11:
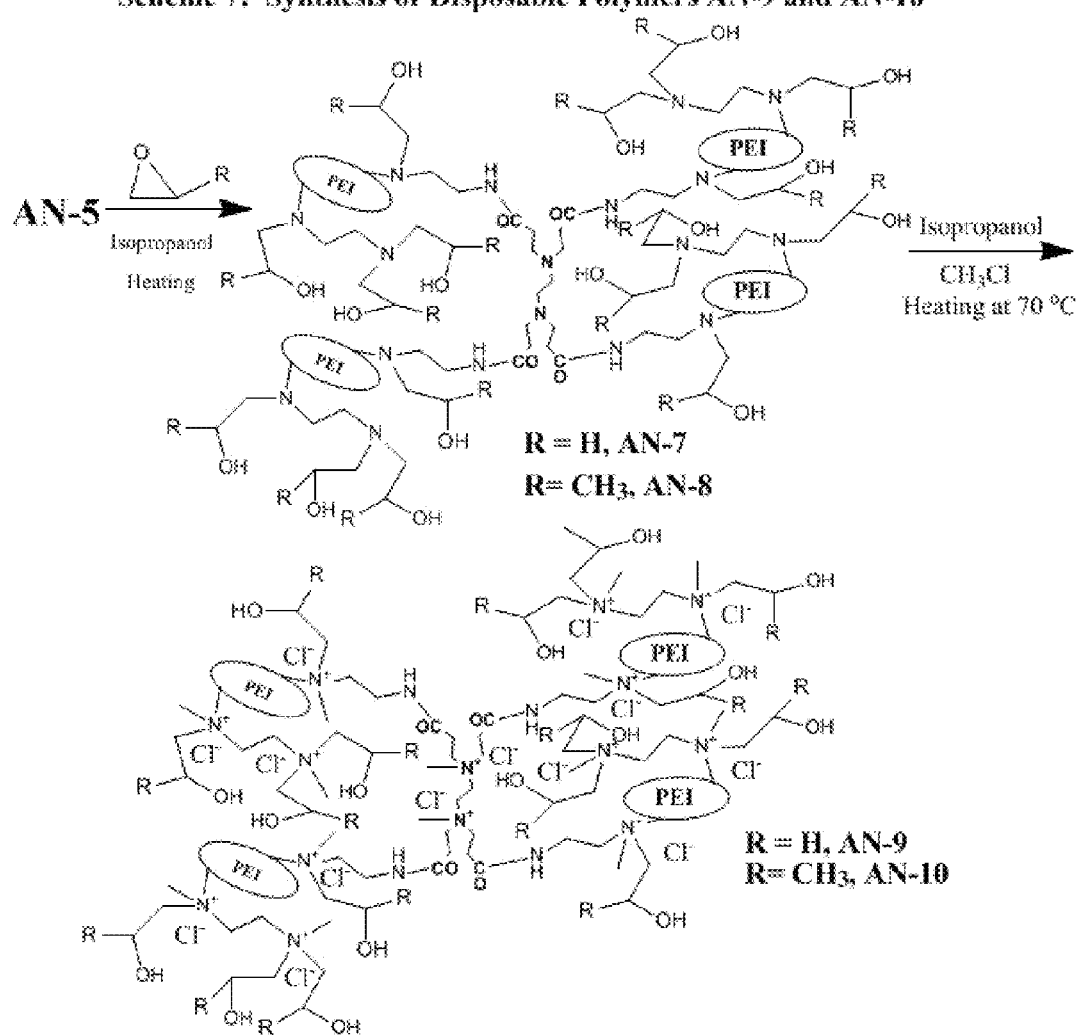
FIG. 11 shows a chemical reaction for synthesis of a class of quaternary amine disposable hyperbranched polymers, specific examples of which are referred to herein as AN-9 and AN-10. This figure also shows non-quaternary products AN-7 and AN-8
Figure 13:
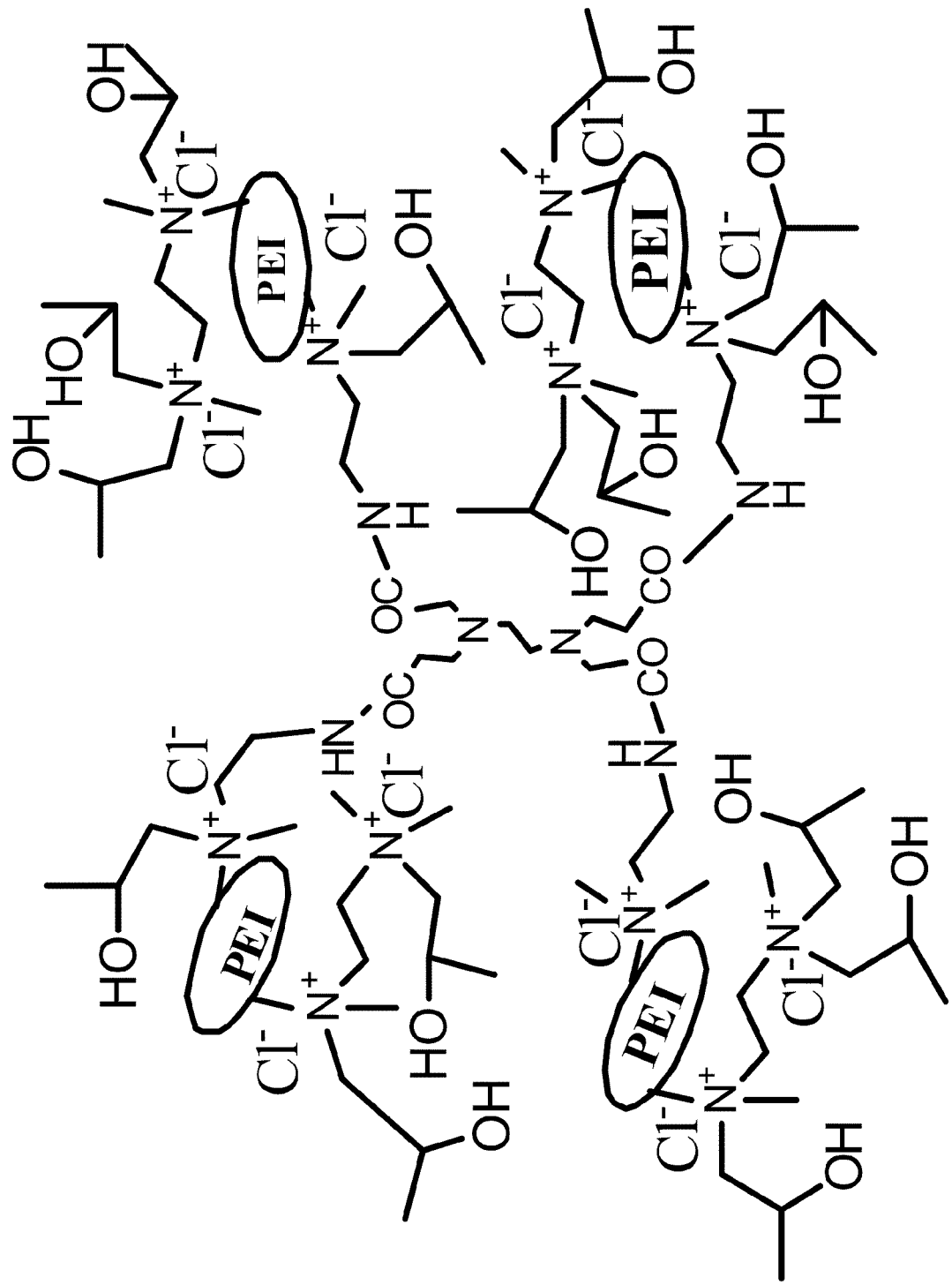
FIG. 13 shows a cross-linked hyperbranched macromolecule comprising quaternary amines, referred to herein as AN-10 and CJ28.

An illustrative example of synthesizing the structure of FIG. 13 and one of the structures shown in FIG. 11 (referred to as AN-10 and CJ28) is as follows: to 300 mL of pressure vessel may be added 20 g of AN-6 (CJ10), 50 mL of isopropanol, 30 g of propylene oxide. The cap may be sealed and heated at an oil bath with temperature at 80° C. for 4 days. After cooling to room temperature, the solvents may be removed through a rotavapor and co-evaporated with 100 mL of toluene. Into this mixture may be added 120 mL of ethanol and 45 mL of dimethyl sulfate and the mixture may be heated 75° C. for 10 min. The pH of the solution may be adjusted to higher than 9.0 by adding 3 N NaOH solution and heating again at the high temperature for another 10 min. The mixture may be cooled to room temperature and diluted by adding 2.5 L of 5% NaCl solution and purified by dialysis using either 10K or 100 K cutoff membrane. The purified material may then be concentrated to give AN-10. A similar method may be followed for producing AN-9, which is also shown in shown in FIG. 11.

Figure 35:
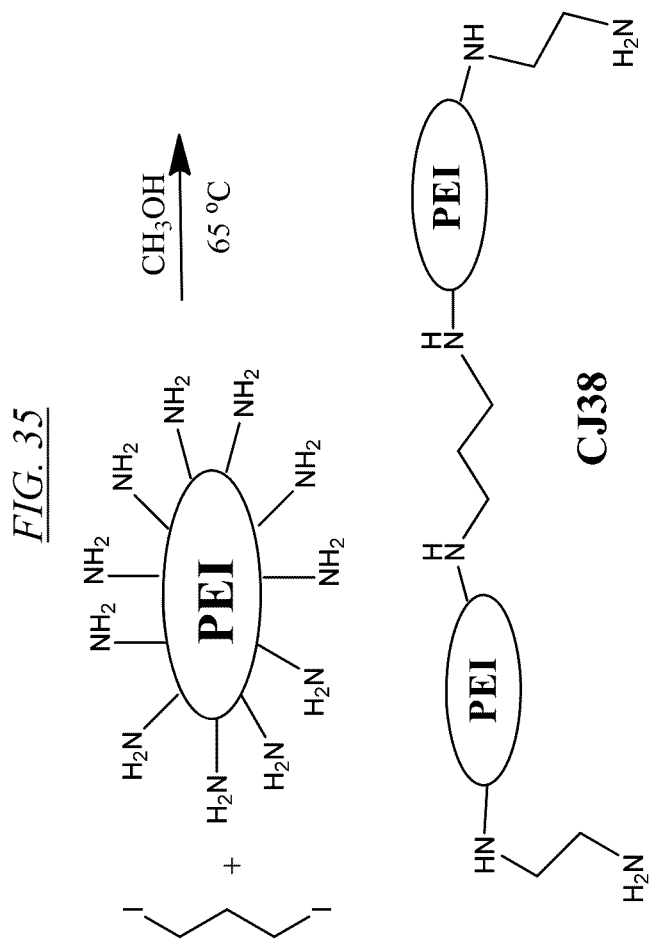
FIG. 35 shows an example of synthesizing a cross-linked hyperbranched macromolecule referred to herein as CJ38.

An illustrative example of synthesizing the structure of FIG. 35 (referred to as CJ38) is as follows: to 30 g of water-free PEI ($M_w$=25,000 in this example, but may vary greatly) in a 250 mL-pressure vessel may be added 100 mL of methanol and 3.0 g of 1.3-diiodopropane and the mixture may be sealed and heated at 65° C. overnight. After cooling to room temperature, the solvents may be removed to give CJ38.

Figure 36:
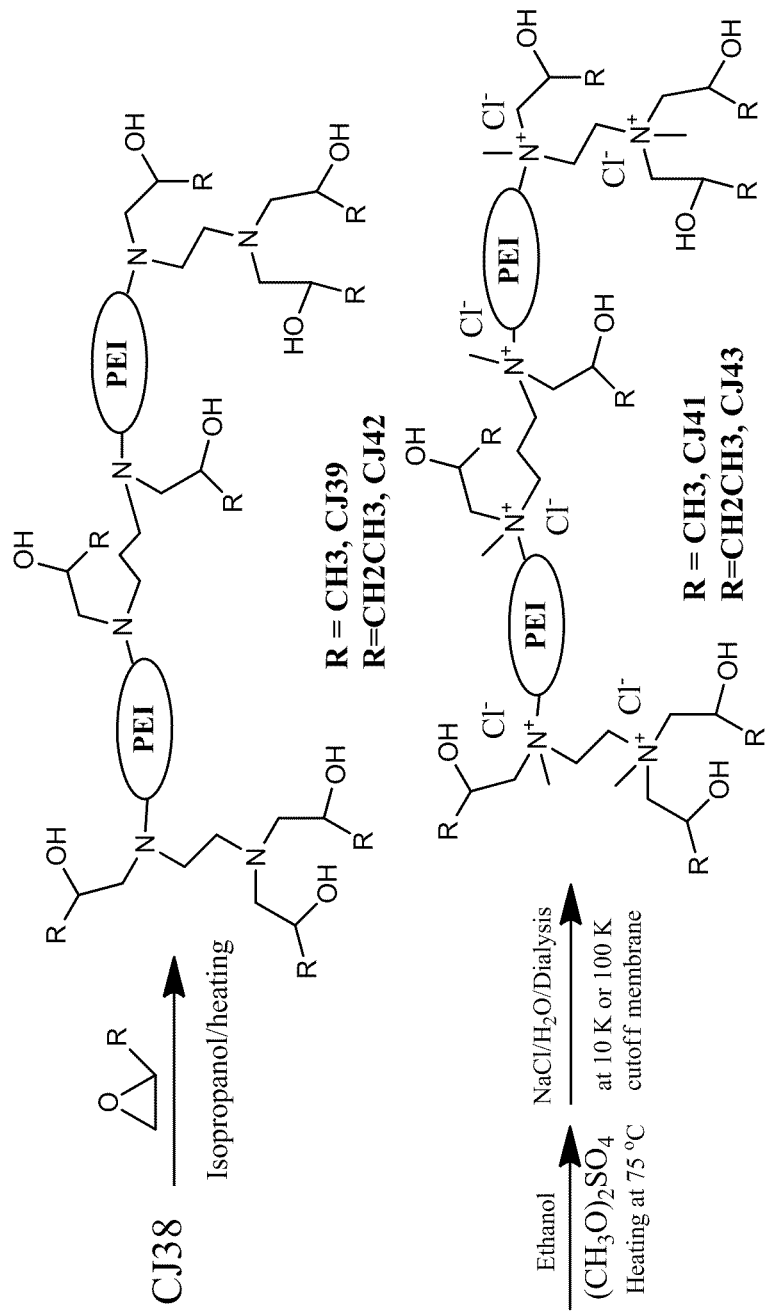
FIG. 36 shows an example of synthesizing quaternary cross-linked hyperbranched macromolecule referred to herein as CJ41 and CJ43. The figure also shows non-quaternary products CJ39 and CJ42.

An illustrative example of synthesizing the molecule known as CJ41, shown in FIG. 36, is as follows: to 300 mL of pressure vessel may be added 30 g of CJ38 and 100 mL of isopropanol and 46 g of propylene oxide. The cap may be sealed and heated at an oil bath with temperature at 80° C. for 2 days. After cooled to room temperature, the solvents may be removed through a rotavapor and co-evaporated with 100 mL of toluene. Into this mixture may be added 120 mL of ethanol and 45 mL of dimethyl sulfate and the mixture may be heated 75° C. for 10 min. The pH of the solution may be adjusted to higher than 9.0 by adding 3 N NaOH solution and heating again at the high temperature for another 10 min. The mixture may be cooled to room temperature and diluted by adding 2.5 L of 5% NaCl solution and purified by dialysis using either 10K or 100 K cutoff membrane. The purified material was concentrated to give CJ41.

An illustrative example of synthesizing the molecule known as CJ43, shown in FIG. 36, is as follows: to 300 mL of pressure vessel may be added 50 g of CJ38 and 100 mL of isopropanol and 80 gm of 1,2-epoxybutane. The cap may be sealed and heated at an oil bath with temperature at 80° C. for 2 days. After cooled to room temperature, the solvents may be removed through a rotavapor and co-evaporated with 100 mL of toluene. Into this mixture may be added 120 mL of ethanol and 50 mL of dimethyl sulfate and the mixture may be heated 75° C. for 10 min. The pH of the solution was adjusted to greater than 9.0 by adding 3 N NaOH solution and heating again at the high temperature for another 10 min. The mixture may then be cooled to room temperature and diluted by adding 2.5 L of 5% NaCl solution and purified by dialysis using either 10K or 100 K cutoff membrane. The purified material may then be concentrated to give CJ43.

As is known in the art, AN-1, AN-2 and AN-3 (see FIG. 2, FIG. 3, FIG. 4, respectively) bind nitrate and bromide at pH 5.0 and release them anions at pH 9.0. However, the pH of the most potable water sources and wastewater effluents is roughly between 6.5 and 8.5. Two example macromolecules (AN-9 and AN-10) may be prepared to selectively bind nitrate, bromide, and other contaminants in both low and high pH solutions. The crosslinked PEI (AN-5) may in one example be reacted with approximately 1.1 equivalent of either ethylene oxide (EO) or propylene oxide (PPO) in isopropanol as solvent in a pressure vessel for approximately three to four days to prepare the reaction intermediates AN-7 or AN-8 in high yields. The tertiary amines of the AN-6 or AN-7 may then be quaternized, for example, with a primary haloalkane such as methyl chloride to yield AN-9 and AN-10. The nitrate/bromide binding capacities of the quaternized PEI macromolecules may be measured at pH 5.0 and 9.0 in deionized water and in low/high ionic strength make-up groundwater. This is to verify that the binding of the new example quaternized macromolecules are less dependent on pH values of water and wastewater.

Figure 14:
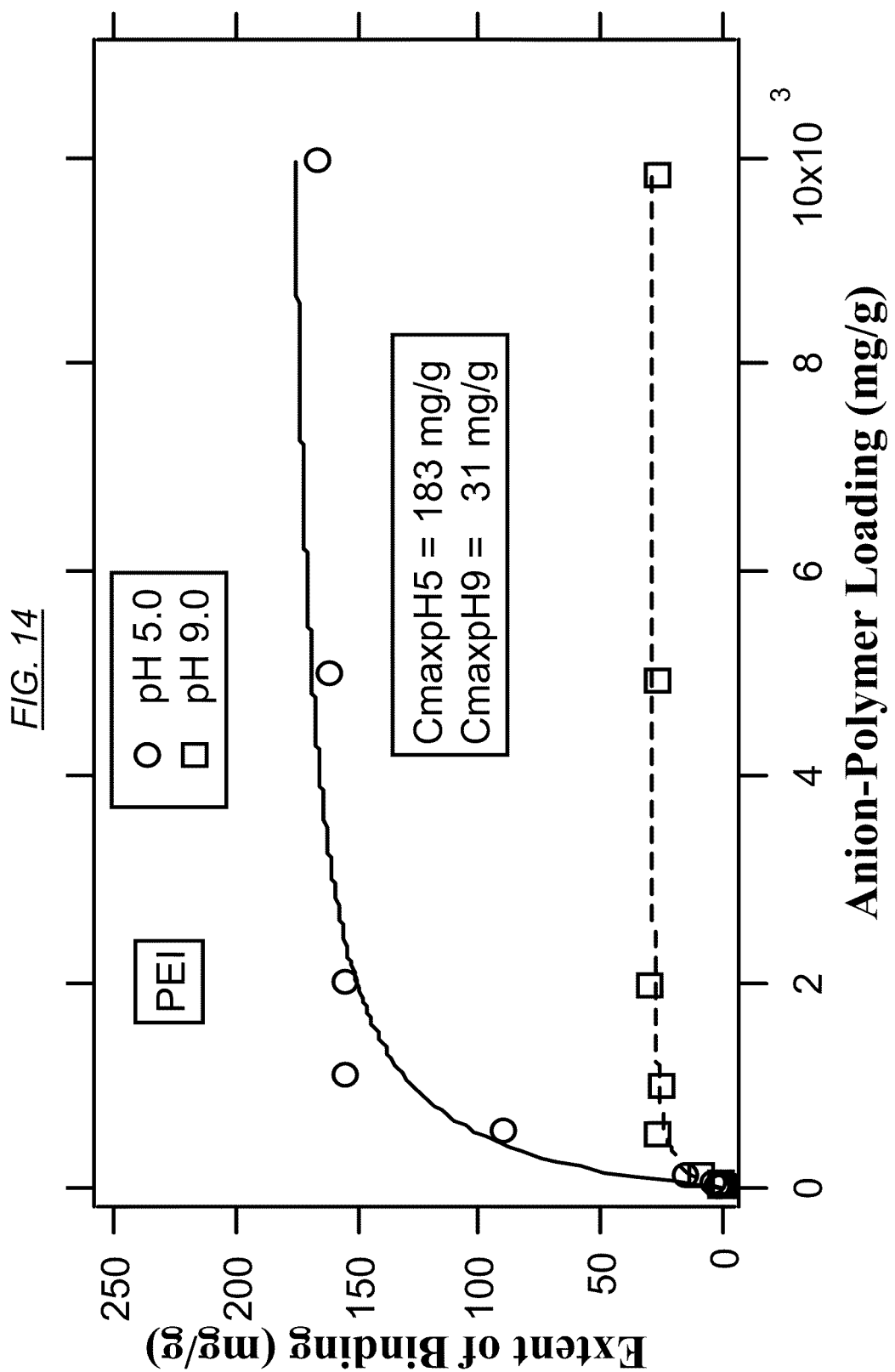
FIG. 14 shows the extent of binding (EOB) at various degrees of bromine-polymer loading for PEI at pH 5 and pH 9.
Figure 15:
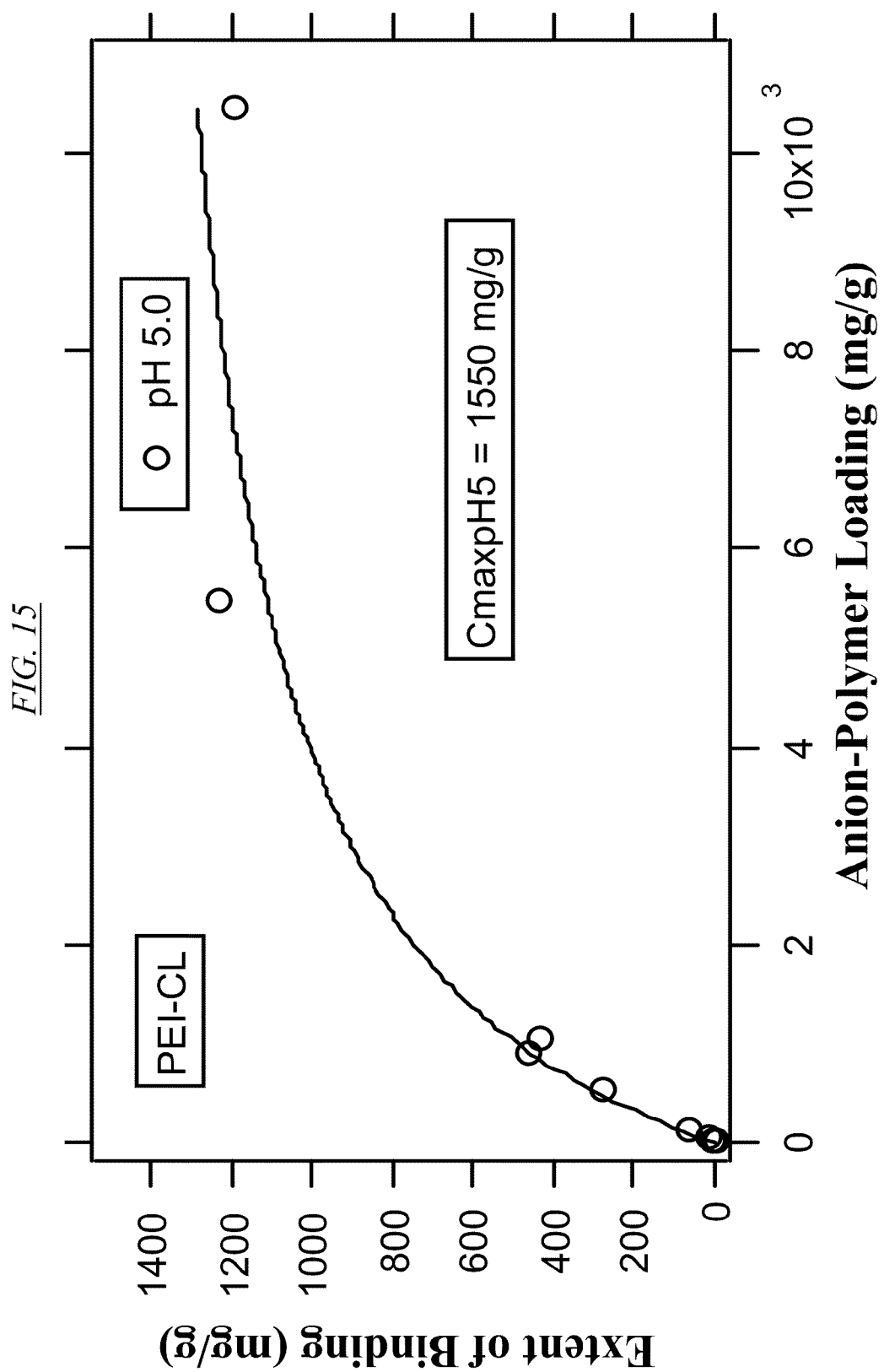
FIG. 15 shows the extent of binding of cross-linked PEI (AN-5) at various degrees of bromine-polymer loading for PEI at pH 5.
Figure 16:
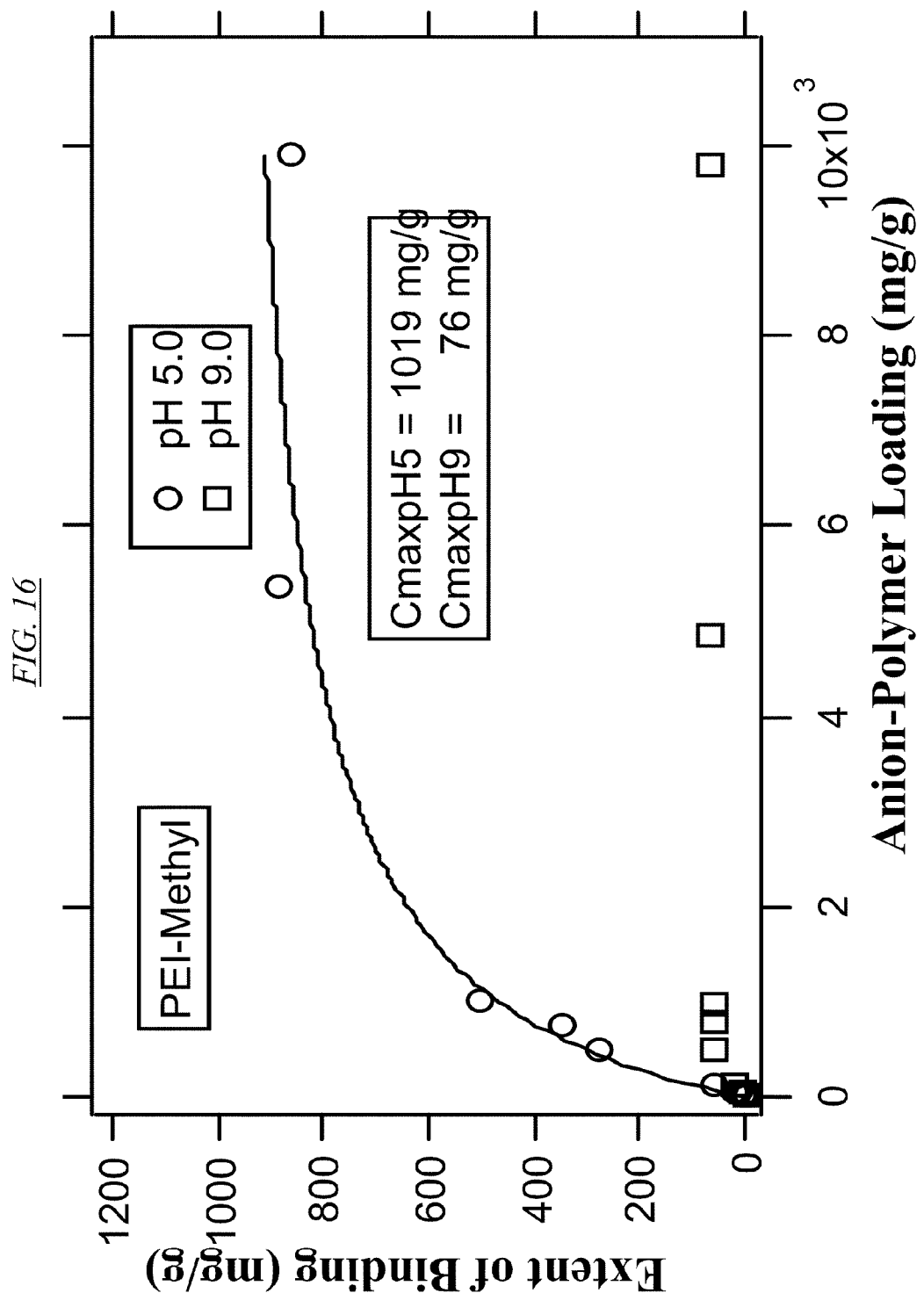
FIG. 16 shows the extent of binding of PEI-Methyl (AN-1) at various degrees of bromine-polymer loading for PEI at pH 5 and pH 9.
Figure 17:
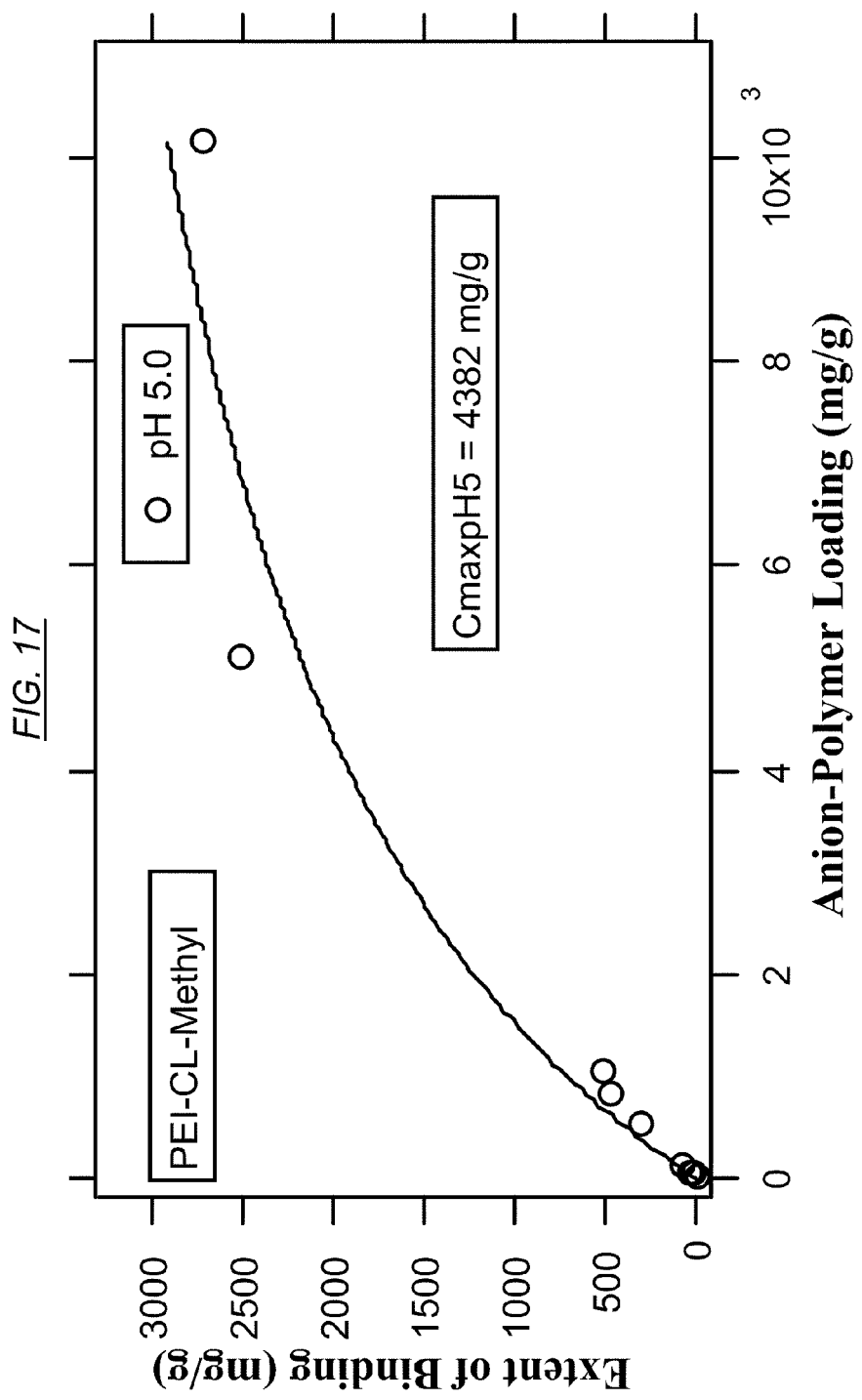
FIG. 17 shows the extent of binding of cross-linked PEI-Methyl (AN-6) at various degrees of bromine-polymer loading for PEI at pH 5.
Figure 18:
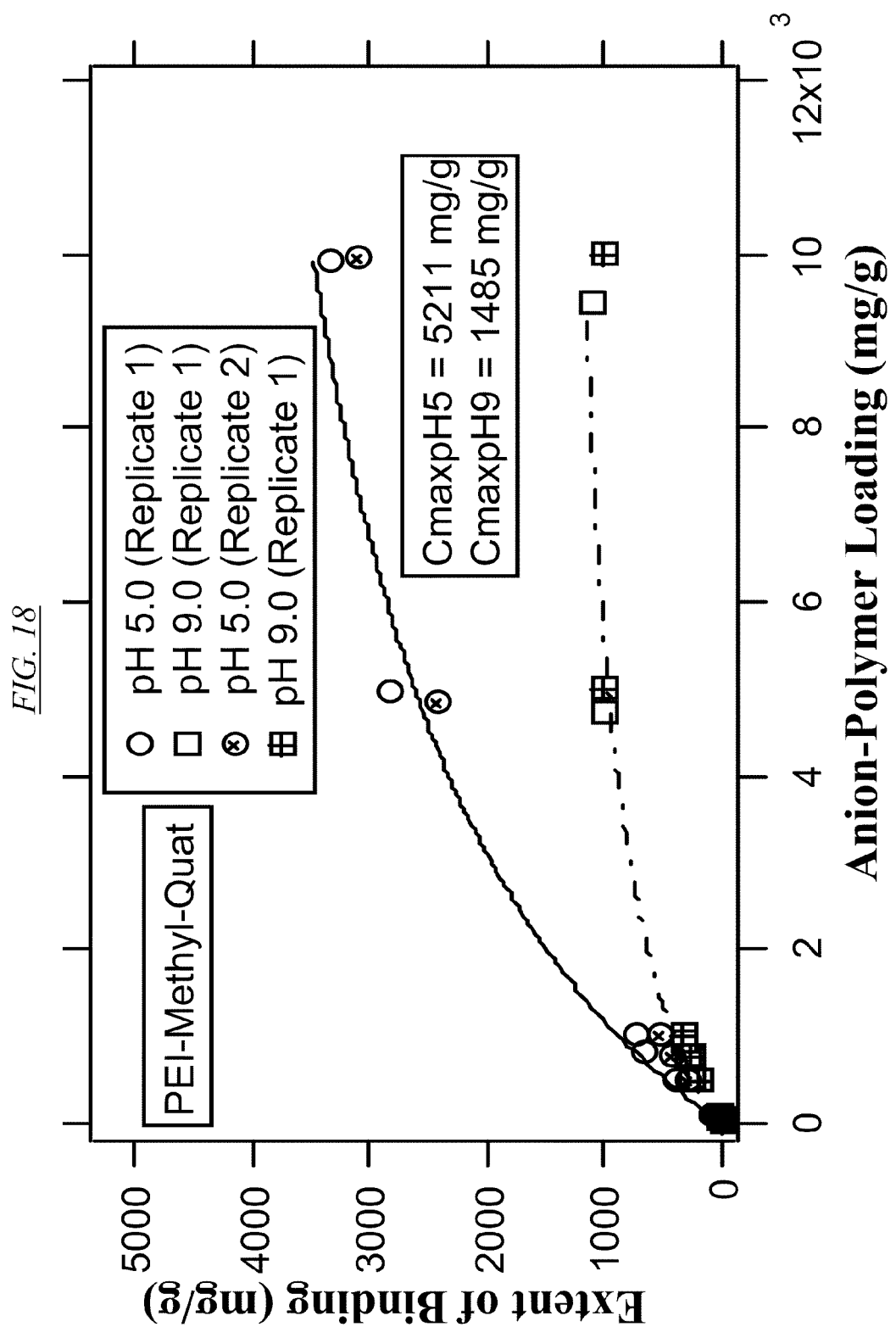
FIG. 18 shows the extent of binding of quaternary PEI functionalized with a methyl group (structure shown in FIG. 9) at various degrees of bromine-polymer loading for PEI at pH 5 and at pH 9.

FIG. 14, FIG. 16, and FIG. 18 are example tables that illustrate the extent of binding between bromine and three non-cross-linked hyperbranched macromolecules, at pH 5 and at pH 9 for comparison. These figures illustrate how the extent of binding can be higher at the lower pH. In embodiments where the macromolecules are to be recycled, bromine therefore may be released at the higher pH. FIG. 15 and FIG. 17 illustrate the binding properties of cross-linked macromolecules with bromine. Comparing FIG. 14 (PEI) with FIG. 15 (AN-5, cross-linked PEI) illustrates that cross-linking may result in a large increase in binding capacity at pH 5.0. A similar comparison may be made between FIG. 16 (non-cross-linked AN-1) and FIG. 17 (cross-linked AN-6). FIG. 16 (which has tertiary amines) and FIG. 18 (comprising quaternary amines, or at least a partial quaternization) shows that even in the absence of cross-linking, quaternization can have a dramatic effect on the binding capacity of bromine.

In FIG. 21 through FIG. 34 are shown illustrations of example nitrate and sulfate binding properties with many of the example quaternized and cross-linked compounds discussed in this disclosure. These examples illustrate that when various quaternized and cross-linked compounds are added to a water stream (either alone or for example in combination with non-cross-linked and non-quaternary macromolecules as shown in FIG. 26 through FIG. 34), they can remove both sulfate and nitrate from the water. In exchange for the takeup of sulfate and nitrate, chlorine that was originally associated with the quaternized molecules dissociates from the molecules and enters solution in the water. FIG. 30 through FIG. 34 also illustrate that CJ40 (also referred to as AN-6 and CJ10) can capture sulfate, but has relatively little effect on nitrate at the high concentrations. Thus, CJ40 may be useful for selectively capturing sulfate.

Bromide removal by reverse osmosis (RO) is expensive due to (i) the high pressure (e.g., about 10-70 bar) required to operate RO membranes and (ii) the number of RO passes (about two or three) usually required to remove bromide to an acceptable level prior to ozonation. However, this disclosure provides means by which bromide may potentially be removed more efficiently. In one illustrative example, a bromide-selective and non-recyclable macromolecule, or more than one such variety of macromolecule, may be added the feed water of an RO unit to eliminate the number of additional RO passes. In another illustrative embodiment, bromide may be recovered from feed water, RO bypass, or permeate by coupling ultrafiltration with a recyclable macromolecule that selectively binds and release through pH change.

It is important to consider at least two particular issues prior to implementing a means to remove bromide from potable water as part of a water treatment system: (i) it is important to evaluate the fouling potential of UF/RO filtration membranes by bromide-selective macromolecules when they are added into the feed water and (ii) it is important to ensure that the bromide-selective polymers do not enter the product water (i.e., permeate) of RO/UF units.

Figure 19:
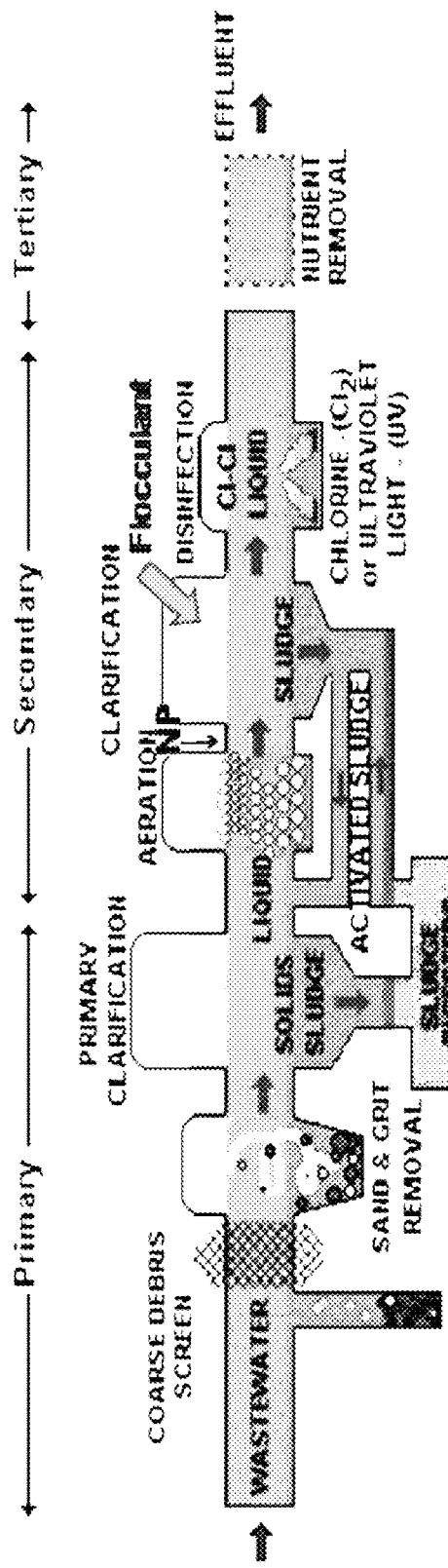
FIG. 19 shows an example of a water treatment process using hyperbranched macromolecules.

FIG. 19 shows a wastewater treatment process where nitrate is removed from the treatment stream at the location represented by "NP," which is after screening, primary clarification phases, and aeration, but prior to a secondary clarification stage and before disinfection. In the secondary clarification stage, hyperbranched macromolecules described in this disclosure may be removed by flocculation and be removed as part of the sludge. It may be useful at this point to introduce a coagulant aid such as, without limitation, polydimethyl diallyammonium chloride (polyDADMAC). See Gabelich, C., Ishida, K. P. and Bold, R. M. (2005) "Testing of Water Treatment Copolymers for Compatibility with Polyamide Reverse Osmosis Membranes," *Environmental Progress* 24: 410-16. This additive may facilitate the incorporation of the complex of nitrate and the branched macromolecule into the sludge of the treatment plant.

In one embodiment, use of branched macromolecules may be limited to certain times a year, such as during the winter when the need is most critical. Therefore, the macromolecules could be prepared and provided as a chemical feed in combination with a flocculent aid, to be used by the treatment plant only when other means do not allow the plant to meet regulatory requirements for water purity.

The above are exemplary modes of carrying out the invention and are not intended to be limiting. While embodiments and applications have been shown and described, it would be apparent to those skilled in the art having the benefit of this disclosure that many more modifications than mentioned above are possible without departing from the inventive concepts disclosed herein. The invention, therefore, and the scope of the appended claims, should not be limited to the embodiments described herein.

What is claimed is:

1. A compound having the formula

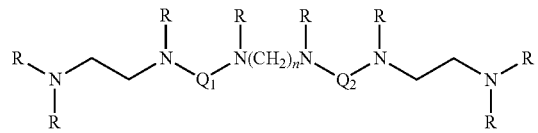

wherein n is an integer from 2 to 5, each of $Q_1$ and $Q_2$ is a moiety comprising a hyperbranched polymer structure, and R is hydrogen, an alkyl group, or a 2-hydroxyalkyl group; and wherein substantially all amines have been quaternized through binding with a quaternary N-substituent.

2. The compound of claim 1, wherein m is 3.

3. The compound of claim 1, wherein the quaternary N-substituent is an alkyl group.

4. A macromolecule having the formula

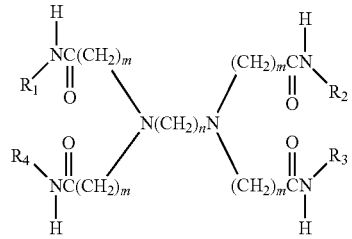

wherein m is an integer from 2 to 5, and n is an integer from 2 to 5; and wherein each of $R_1$, $R_2$, $R_3$, and $R_4$ is a moiety comprising a hyperbranched polymer structure; and wherein within each hyperbranched polymer structure, substantially all amines have been quaternized through binding with a first N-substituent.

5. The macromolecule of claim 4, wherein each of $R_1$, $R_2$, $R_3$, and $R_4$ comprises hyperbranched polyethyleneimine (PEI).

6. The macromolecule of claim 4, wherein each of $R_1$, $R_2$, $R_3$, and $R_4$ comprises a hyperbranched polymer structure derived from polyethyleneimine (PEI) wherein substantially all hydrogen atoms on the original primary and secondary amines have been replaced by a second N-substituent.

7. The macromolecule of claim 6, wherein the first N-substituent is selected from the group consisting of an alkyl group and a 2-hydroxyalkyl group.

8. The macromolecule of claim 7, wherein the first N-substituent is selected from the group consisting of methyl and ethyl.

9. A macromolecule having the formula

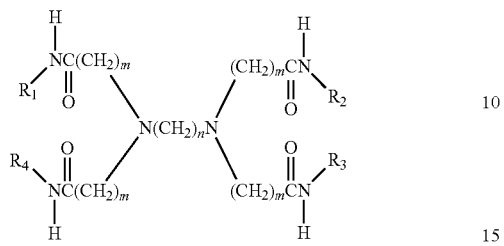

wherein m is an integer from 2 to 5, and n is an integer from 2 to 5;

wherein each of $R_1$, $R_2$, $R_3$ and $R_4$ is a moiety comprising a hyperbranched polymer structure derived from polyethyleneimine (PEI) wherein substantially all hydrogen atoms on the original primary and secondary amines have been replaced by a first N-substituent; and wherein the first N-substituent is selected from the group consisting of 2-hydroxyethyl, 2-hydroxypropyl, and 2-hydroxybutyl.

10. The macromolecule of claim 4, wherein m and n are 2.

11. The macromolecule of claim 4, wherein the first N-substituent is an alkyl group.

\* \* \* \* \*